(12) United States Patent (10) Patent No.: US 9,017,413 B2
Siegal et al. (45) Date of Patent: Apr. 28, 2015

(54) EXPANDING IMPLANT FOR INSERTION BETWEEN TWO REGIONS OF TISSUE AND CORRESPONDING METHOD

(71) Applicant: NLT Spine Ltd., Kfar Saba (IL)

(72) Inventors: Tzony Siegal, Moshav Shoeva (IL); Oded Loebl, Tel Mond (IL); Didier Toubia, Raanana (IL)

(73) Assignee: NLT Spine Ltd., Kfar Saba (IL)

( * ) Notice: Subject to any disclaimer, the term of this patent is extended or adjusted under 35 U.S.C. 154(b) by 0 days.

(21) Appl. No.: 13/941,550

(22) Filed: Jul. 15, 2013

(65) Prior Publication Data

US 2013/0304214 A1 Nov. 14, 2013

Related U.S. Application Data

(63) Continuation of application No. 13/654,463, filed on Oct. 18, 2012, now Pat. No. 8,777,993, which is a continuation-in-part of application No. PCT/IB2011/053143, filed on Jul. 14, 2011.

(60) Provisional application No. 61/652,345, filed on May 29, 2012, provisional application No. 61/707,963, filed on Sep. 30, 2012.

(51) Int. Cl.
*A61F 2/44* (2006.01)
*A61F 2/46* (2006.01)
(Continued)

(52) U.S. Cl.
CPC .................. *A61F 2/442* (2013.01); *A61F 2/447* (2013.01); *A61F 2/4611* (2013.01); *A61B 17/7065* (2013.01); *A61F 2002/2817* (2013.01); *A61F 2002/2835* (2013.01); *A61F 2002/30092* (2013.01); *A61F 2002/30126* (2013.01); *A61F 2002/30153* (2013.01);
(Continued)

(58) Field of Classification Search
CPC ....... A61F 2/4455; A61F 2/4425; A61F 2/44; A61B 17/025; A61B 2017/0256; A61B 17/1671; A61B 17/1757
USPC ...................... 623/17.11–17.16; 606/90, 105, 606/246–263
See application file for complete search history.

(56) References Cited

U.S. PATENT DOCUMENTS 5,059,193 A 10/1991 Kuslich
5,171,278 A * 12/1992 Pisharodi ...................... 128/898
(Continued)

FOREIGN PATENT DOCUMENTS

WO 98/34552 8/1998

*Primary Examiner* — Jerry Cumberledge
(74) *Attorney, Agent, or Firm* — Mark M. Friedman

(57) ABSTRACT

A laterally deflectable asymmetric implant for implanting into a body may comprise a deflectable piece having distal and proximal ends and assuming a straightened insertion state. The backbone may abut or interconnect with said deflectable piece at the distal end of the deflectable piece. In a fully deflected state the implant may define an asymmetric shape, e.g. a D-shaped loop, defining an at least partially enclosed volume. The deflectable piece may comprise a sequence of segments interconnected at effective hinges. Longitudinal pressure applied to the proximal end of the deflectable piece (or applied to the backbone in an opposite direction) may cause relative longitudinal movement between the backbone and the proximal end of the deflectable piece and may generate outward horizontal movement of the deflectable piece away from the backbone. In one embodiment, the implant is implanted using lateral access into an anterior zone of a vertebra and deployed posteriorly.

18 Claims, 26 Drawing Sheets

(51) Int. Cl.
   *A61B 17/70*   (2006.01)
   *A61F 2/28*    (2006.01)
   *A61F 2/30*    (2006.01)

(52) U.S. Cl.
   CPC ........ *A61F 2002/30156* (2013.01); *A61F 2002/30158* (2013.01); *A61F 2002/30186* (2013.01); *A61F 2002/30187* (2013.01); *A61F 2002/302* (2013.01); *A61F 2002/30202* (2013.01); *A61F 2002/30266* (2013.01); *A61F 2002/30304* (2013.01); *A61F 2002/30382* (2013.01); *A61F 2002/30401* (2013.01); *A61F 2002/30431* (2013.01); *A61F 2002/30462* (2013.01); *A61F 2002/30471* (2013.01); *A61F 2002/30476* (2013.01); *A61F 2002/30484* (2013.01); *A61F 2002/30492* (2013.01); *A61F 2002/305* (2013.01); *A61F 2002/30504* (2013.01); *A61F 2002/30512* (2013.01); *A61F 2002/3054* (2013.01); *A61F 2002/3055* (2013.01); *A61F 2002/30556* (2013.01); *A61F 2002/30579* (2013.01); *A61F 2002/30601* (2013.01); *A61F 2002/30624* (2013.01); *A61F 2002/30785* (2013.01); *A61F 2002/30904* (2013.01); *A61F 2002/4415* (2013.01); *A61F 2002/4475* (2013.01); *A61F 2002/448* (2013.01); *A61F 2002/4627* (2013.01); *A61F 2002/4628* (2013.01); *A61F 2002/4629* (2013.01); *A61F 2002/4679* (2013.01); *A61F 2310/00017* (2013.01); *A61F 2310/00023* (2013.01); *A61F 2310/00029* (2013.01)

(56) References Cited

U.S. PATENT DOCUMENTS

| | | | |
|---|---|---|---|
| 6,039,761 A * | 3/2000 | Li et al. | 623/17.16 |
| 6,126,689 A | 10/2000 | Brett | |
| 6,190,414 B1 | 2/2001 | Young et al. | |
| 6,375,682 B1 | 4/2002 | Fleischmann et al. | |
| 6,419,705 B1 | 7/2002 | Erickson | |
| 6,582,451 B1 * | 6/2003 | Marucci et al. | 606/207 |
| 6,830,589 B2 | 12/2004 | Erickson | |
| 7,087,055 B2 | 8/2006 | Lim et al. | |
| 7,097,648 B1 | 8/2006 | Globerman et al. | |
| 7,625,377 B2 * | 12/2009 | Veldhuizen et al. | 606/90 |
| 7,799,081 B2 | 9/2010 | McKinley | |
| 7,846,206 B2 * | 12/2010 | Oglaza et al. | 623/17.11 |
| 7,901,409 B2 * | 3/2011 | Canaveral et al. | 606/86 R |
| 7,947,078 B2 | 5/2011 | Siegal | |
| 7,959,652 B2 * | 6/2011 | Zucherman et al. | 606/249 |
| 8,021,429 B2 | 9/2011 | Viker | |
| 8,025,697 B2 | 9/2011 | McClellan, III et al. | |
| 8,062,375 B2 | 11/2011 | Glerum et al. | |
| 8,105,382 B2 * | 1/2012 | Olmos et al. | 623/17.15 |
| 8,133,232 B2 * | 3/2012 | Levy et al. | 606/90 |
| 8,187,332 B2 * | 5/2012 | McLuen | 623/17.16 |
| 8,292,963 B2 | 10/2012 | Miller et al. | |
| 8,303,658 B2 | 11/2012 | Peterman | |
| 8,308,802 B2 | 11/2012 | Rhoda et al. | |
| 8,317,798 B2 | 11/2012 | Lim et al. | |
| 8,317,802 B1 | 11/2012 | Manzi et al. | |
| 8,317,866 B2 | 11/2012 | Palmatier et al. | |
| 8,323,344 B2 * | 12/2012 | Galley et al. | 623/17.16 |
| 8,337,531 B2 | 12/2012 | Johnson et al. | |
| 8,337,559 B2 | 12/2012 | Hanseel et al. | |
| 8,343,193 B2 | 1/2013 | Johnson et al. | |
| 8,349,013 B2 | 1/2013 | Zucherman et al. | |
| 8,349,014 B2 | 1/2013 | Barreiro et al. | |
| 8,382,842 B2 * | 2/2013 | Greenhalgh et al. | 623/17.16 |
| 8,398,713 B2 | 3/2013 | Weiman | |
| 8,628,576 B2 * | 1/2014 | Triplett et al. | 623/17.11 |
| 8,628,577 B1 * | 1/2014 | Jimenez | 623/17.15 |
| 8,814,937 B2 * | 8/2014 | Mayer | 623/17.12 |
| 2004/0133280 A1 * | 7/2004 | Trieu | 623/17.16 |
| 2005/0261683 A1 * | 11/2005 | Veldhuizen et al. | 606/61 |
| 2005/0278036 A1 * | 12/2005 | Leonard et al. | 623/23.47 |
| 2006/0235423 A1 * | 10/2006 | Cantu | 606/90 |
| 2008/0243255 A1 | 10/2008 | Buttler | |
| 2009/0222100 A1 * | 9/2009 | Cipoletti et al. | 623/17.16 |
| 2010/0131009 A1 * | 5/2010 | Roebling et al. | 606/249 |
| 2010/0211176 A1 * | 8/2010 | Greenhalgh | 623/17.15 |
| 2011/0276141 A1 * | 11/2011 | Caratsch | 623/17.16 |
| 2011/0319997 A1 | 12/2011 | Glerum et al. | |
| 2012/0004732 A1 * | 1/2012 | Goel et al. | 623/17.16 |
| 2012/0123546 A1 * | 5/2012 | Medina | 623/17.16 |
| 2013/0066374 A1 * | 3/2013 | Galley et al. | 606/249 |

* cited by examiner

| METHOD - 100 |
|---|

| INSERTING THE IMPLANT INTO AN ANTERIOR PORTION OF THE BODY USING LATERAL ACCESS WHILE THE IMPLANT IS IN A STRAIGHTENED OR LOW CURVATURE STATE, THE IMPLANT HAVING A BACKBONE AND A DEFLECTABLE PIECE MEETING THE BACKBONE AT A DISTAL END OF THE DEFLECTABLE PIECE |
|---|

↓ 110

| DEPLOYING THE IMPLANT POSTERIORLY BY DEFLECTING THE DEFLECTABLE PIECE |
|---|

```
┌─────────────────────────────┐
│       METHOD - 300          │
└─────────────────────────────┘

┌──────────────────────────────────────────────────────┐
│   INSERTING THE IMPLANT INTO THE BODY WHILE THE      │
│   IMPLANT IS IN A STRAIGHTENED OR LOW CURVATURE      │
│   STATE, THE IMPLANT HAVING A BACKBONE AND A         │
│   DEFLECTABLE PIECE COMPRISING A SEQUENCE OF         │
│   SEGMENTS INTERCONNECTED AT EFFECTIVE HINGES        │
└──────────────────────────────────────────────────────┘
                                              ⎬310

┌──────────────────────────────────────────────────────┐
│   HAVING A DISTAL SEGMENT OF THE SEQUENCE MEET THE   │
│   BACKBONE AT A DISTAL END OF THE DEFLECTABLE PIECE  │
└──────────────────────────────────────────────────────┘
                                              ⎬320

┌──────────────────────────────────────────────────────┐
│   FORMING AN ASYMMETRIC LOOP BETWEEN THE BACKBONE    │
│   AND DEFLECTABLE PIECE TOGETHER BY DEFLECTING THE   │
│   DEFLECTABLE PIECE SUCH THAT A PROXIMAL END OF THE  │
│   DEFLECTABLE PIECE MOVES LONGITUDINALLY RELATIVE TO │
│   AT LEAST A DISTAL END OF THE BACKBONE AND          │
│   INTERCONNECTS TO THE BACKBONE                      │
└──────────────────────────────────────────────────────┘
                                              ⎬330
```

FIG. 18

| METHOD - 400 |

| INSERTING INTO THE BODY A FIRST LATERALLY DEFLECTABLE IMPLANT THAT HAS A FIRST BACKBONE AND A FIRST DEFLECTABLE PIECE WHILE THE FIRST DEFLECTABLE PIECE IS IN A STRAIGHTENED OR LOW CURVATURE INSERTION STATE |

↓ 410

| INSERTING INTO THE BODY A SECOND LATERALLY DEFLECTABLE IMPLANT THAT HAS A SECOND BACKBONE AND A SECOND DEFLECTABLE PIECE WHILE THE SECOND DEFLECTABLE PIECE IS IN A STRAIGHTENED OR LOW CURVATURE INSERTION STATE AND SUCH THAT THE FIRST AND SECOND BACKBONES ARE SUBSTANTIALLY PARALLEL |

↓ 420

| DEFLECTING THE FIRST AND SECOND LATERALLY DEFLECTABLE IMPLANTS IN OPPOSITE DIRECTIONS SUCH THAT THE FIRST LATERALLY DEFLECTABLE IMPLANT DEFINES A FIRST ASYMMETRIC LOOP, SAID FIRST ASYMMETRIC LOOP DEFINES AN AT LEAST PARTIALLY ENCLOSED VOLUME AND SUCH THAT THE SECOND LATERALLY DEFLECTABLE IMPLANT DEFINES A SECOND ASYMMETRIC LOOP, SAID SECOND ASYMMETRIC LOOP DEFINES AN AT LEAST PARTIALLY ENCLOSED VOLUME |

| METHOD - 500 |
|---|

| INSERTING AN IMPLANT INTO A BODY WHILE THE IMPLANT IS IN A STRAIGHTENED OR LOW CURVATURE STATE, THE IMPLANT HAVING A BACKBONE AND A DEFLECTABLE PIECE MEETING THE BACKBONE |
|---|

↳ 510

↓

| GENERATING RELATIVE LONGITUDINAL MOVEMENT BETWEEN A PROXIMAL END OF THE DEFLECTABLE PIECE AND AT LEAST A DISTAL END OF THE BACKBONE SO AS TO DEFLECT THE DEFLECTABLE PIECE AND DISTRACT AN INTERVERTEBRAL SPACE BETWEEN THE FIRST AND SECOND VERTEBRAE |
|---|

EXPANDING IMPLANT FOR INSERTION BETWEEN TWO REGIONS OF TISSUE AND CORRESPONDING METHOD

PRIORITY INFORMATION

The present U.S. Patent Application is a continuation of U.S. patent application Ser. No. 13/654,463 filed 18 Oct. 2012 which is a continuation-in-part of PCT/IB2011/053143 international patent application filed 14 Jul. 2011. U.S. patent application Ser. No. 13/654,463 filed 18 Oct. 2012 is also the non-provisional of (i) U.S. provisional patent application No. 61/707,963 filed 30 Sep. 2012, and (ii) U.S. provisional patent application No. 61/652,345 filed 29 May 2012, each filed by Applicants herein.

FIELD AND BACKGROUND OF THE INVENTION

The present invention generally relates to apparatus and methods for implants, and more particularly to apparatus and methods for implanting deflectable implants.

Minimally invasive and percutaneous subcutaneous procedures, which are performed through a small orifice in the skin, limit the size of the surgery tools and implants that are used. Hence it would be highly advantageous to develop implants that have small cross sections such that they can be inserted easily through a small orifice in the skin and be formed into their final functional expanded shape at the intended implantation site in the body. It would be highly advantageous to provide implants for spinal surgeries such as interbody fusion, motion preservation and vertebral augmentation that may be inserted into the body in minimally invasive procedures.

In addition, precise control over the location of an implant is vitally important to the success or failure of a spinal surgery. Undesired movement of the implant after placement, imprecise placement, improper or imprecise opening, expanding or other forming of the implant after insertion can result in the implant not being precisely where the user intended the implant to be and imperfect fusion. Differences of a millimeter can change an otherwise successful surgery into an unsuccessful surgery. Many prior art methods and apparatuses have been developed to control the exact placement and opening of implants, such as those used in surgery, for example spinal surgery. There is a compelling need for an implant and a method of its implantation that provides the greatest clinical benefit and allows the user to have precise control over the insertion, deployment and follow-up positioning and use of the implant.

Furthermore, there is a need for alternative approaches to insertion of implants into the body, for example in spinal surgery, since approaches through the front have disadvantages, for example since they require moving vital organs.

SUMMARY OF THE PRESENT INVENTION

One aspect of the present invention is a laterally deflectable implant for implanting into a body, comprising a deflectable piece having a distal end and a proximal end and assuming a straightened or low curvature insertion state for insertion into the body; and a backbone configured to interconnect with or abut the deflectable piece, the deflectable piece in a fully deflected state defining, together with said backbone, an asymmetric loop wherein said asymmetric loop defines an at least partially enclosed volume, wherein longitudinal movement of the proximal end of the deflectable piece relative to at least a distal end of the backbone deflects the deflectable piece to the deflected state to form, with said backbone, the asymmetric loop, wherein the implant in a deflected state is asymmetric such that the implant does not have an axis of symmetry parallel to the backbone.

A further aspect of the present invention is a method of implanting an implant into a body, comprising inserting the implant into an anterior portion of the body using lateral access while the implant is in a straightened or low curvature state, the implant having a backbone and a deflectable piece meeting the backbone at a distal end of the deflectable piece; and deploying the implant posteriorly by deflecting the deflectable piece.

A still further aspect of the present invention is a method of implanting an implant into a body, comprising inserting the implant into the body while the implant is in a straightened or low curvature state, the implant having a backbone and a deflectable piece, the backbone comprising a beam; anchoring the implant by situating the backbone on a cortical bone so that the backbone holds at least a majority of a load on the implant; and guiding the deflectable piece by holding the backbone stationary while applying longitudinal pressure to a proximal end of the deflectable piece so as to deflect the deflectable piece such that the deflectable piece together with the backbone form an asymmetric loop, the asymmetric loop defining an at least partially enclosed volume.

A yet still further aspect of the present invention is a method of implanting an implant into a body, comprising inserting the implant into the body while the implant is in a straightened or low curvature state, the implant having a backbone and a deflectable piece comprising a sequence of segments interconnected at effective hinges; having a distal segment of the sequence meet the backbone at a distal end of the deflectable piece; and forming an asymmetric loop between the backbone and deflectable piece together by deflecting the deflectable piece such that a proximal end of the deflectable piece moves longitudinally relative to at least a distal end of the backbone and interconnects to the backbone.

A still further aspect of the present invention is a method of implanting implants into a body, comprising inserting into the body a first laterally deflectable implant that has a first backbone and a first deflectable piece while the first deflectable piece is in a straightened or low curvature insertion state; inserting into the body a second laterally deflectable implant that has a second backbone and a second deflectable piece while the second deflectable piece is in a straightened or low curvature insertion state and such that the first and second backbones are substantially parallel; deflecting the first and second laterally deflectable implants in opposite directions such that the first laterally deflectable implant defines a first asymmetric loop, said first asymmetric loop defines an at least partially enclosed volume and such that the second laterally deflectable implant defines a second asymmetric loop, said second asymmetric loop defines an at least partially enclosed volume.

A yet still further aspect of the present invention is a method of distracting intervertebral space between a first vertebra and a second vertebra, comprising inserting an implant into a body while the implant is in a straightened or low curvature state, the implant having a backbone and a deflectable piece meeting the backbone; and generating relative longitudinal movement between a proximal end of the deflectable piece and at least a distal end of the backbone so as to deflect the deflectable piece and distract an intervertebral space between the first and second vertebrae.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein:

FIG. 16 is a flow chart showing a method in accordance with one embodiment of the present invention;

FIG. 18 is a flow chart showing a still further method in accordance with one embodiment of the present invention;

FIG. 19 is a flow chart showing a further method in accordance with one embodiment of the present invention;

FIG. 20 is a flow chart showing a still further method in accordance with one embodiment of the present invention;

DETAILED DESCRIPTION OF THE INVENTION

Figure 1:
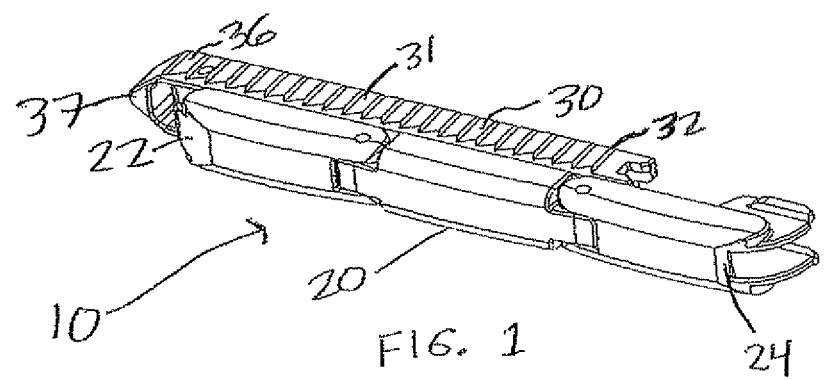
FIG. 1 is an isometric view of an implant in a straightened configuration for example prior to insertion into a body or after insertion but prior to deflection, in accordance with one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a method and apparatus for laterally deflectable implants, and systems and methods for implanting deflectable implants having a loop structure in a human or animal body which may be asymmetric, for example D-shaped, in a deflected state. The implant may during its delivery assume a straightened or low-curvature configuration to facilitate delivery via a minimally invasive procedure. The implant may have a deflectable piece having a distal end and a proximal end and may have a backbone configured to meet (i.e. to abut or interconnect with) the distal end or the proximal end. The deflectable piece may be comprised of a sequence of two or more segments that may be interconnected to one another by effective hinges. The effective hinges may be integral hinges such as lateral cutouts that close upon deflection or the effective hinges may be actual mechanical hinges between the segments. The deflectable piece may be interconnected with the backbone at the distal end and/or at the proximal end of the deflectable piece. If the deflectable piece is connected to the backbone at the distal end of the deflectable piece prior to deflection, then upon deflection, the deflectable piece may also be interconnected with said backbone at the proximal end of the deflectable piece. In a deflected state, for example a fully deflected state, the deflectable piece may define, together with said backbone, an asymmetric loop that defines an at least partially enclosed volume. To deflect, either longitudinal pressure may be applied to the proximal end of the deflectable piece or to the backbone so as to generate relative longitudinal movement between the proximal end and at least a distal end of the backbone. This may generate an outward horizontal movement of at least a central portion of the deflectable piece away from the backbone. The implant may be asymmetric about an axis defined by the direction of insertion and running from the proximal and distal ends and situated between the backbone and the deflectable piece.

In certain embodiments, the implant is arranged to open towards one side of the axis defined by the direction of insertion, and may be asymmetrical about that axis, as will be exemplified below.

In the context of the present description and claims, the word "loop" is used to refer to any structure in which following along the contiguous structure can lead back to the starting point while encircling at least one point lying outside the device, except that there may be a gap between a proximal end (or a distal end) of the deflectable piece and the backbone, most often the proximal end (or the distal end) of the backbone. Typically, and in one preferred embodiment, any such gap does not exceed 10% of a length of the backbone (in the case of telescoping backbones, the length of the backbone when the implant is fully deflected). In other preferred embodiments, the loop is called a modified loop or asymmetric modified loop and, if there is a gap between a proximal end (or a distal end) of the deflectable piece and the backbone, any such gap does not exceed 15% or 20% or 25% or 50% or 75% of such length, depending upon the embodiment. In the event a modified loop is used, such modified loop may be used in conjunction with any other compatible feature or step of the present invention. In certain cases, completion of the loop may be in the form of a sliding joint. The word "loop" does not carry any implication of a circular or smooth shape, although such shapes are in certain cases preferred implementations of the loop structure when open. In still other preferred embodiments, the word "strict loop" is used to refer to any structure in which following along the contiguous structure can lead back to the starting point while encircling at least one point lying outside the device. Embodiments featuring strict loops may be used in conjunction with any other compatible feature or step of the present invention The term "low curvature" insertion state refers to a configuration of the deflectable piece of the implant in which at least one dimension of the deflectable piece, for example the width, other than the longitudinal dimension (i.e. the direction of elongation) of the implant, is significantly reduced, typically to less than 50% (and in some other preferred embodiments to less than 30% or in other preferred embodiments to less than 10%) of the corresponding dimension in its fully deflected state, in order to facilitate delivery through a small orifice. Note that a "straightened configuration" would not be reduced to 0% of the corresponding dimension due to the inherent width of the deflectable piece, even when not deflected at all. In the present context, moreover, the implant, which may comprise the deflectable piece and the backbone together, has a "low-profile" configuration in which preferably two transverse dimensions are small compared to the direction of elongation of the implant, for easy delivery in a minimally invasive procedure, and the implant device opens up in one or two transverse dimensions when deployed.

Particularly preferred but non-limiting examples of implementations include intervertebral implants for supplementing, supporting or replacing an intervertebral disc as part of a fusion procedure or as a motion preserving implant, and intravertebral implants for supporting or restoring a vertebral body. The deflectable implants may include a sequence of segments interconnected with effective hinges (such as conventional hinges or integral hinges) or may be formed with at least an elongated side without clearly distinguished segments.

According to certain embodiments of the present invention, the deflectable piece may comprise a sequence of segments. While a "sequence" means at least two segments, more preferably the sequence includes at least three, and in many preferred cases four or more segments. The segments may be interconnected at effective hinges, the sequence assuming a straightened or low curvature insertion state for insertion into the body, and being deflectable to a deflected state, for example a fully deflected state, that may be defined by abutment of abutment features of adjacent of the segments.

According to certain embodiments of the present invention, an implant for interbody fusion is disclosed. The implant may be deflectable to a deflected loop, for example a fully deflected loop, inside the body, where the loop defines an enclosed volume (or an at least partially enclosed volume, for example if the loop is not a strict loop and has a gap) with the upper and lower surfaces of the body. The implant for interbody fusion further includes at least one opening in one or both of the elongated sides allowing access to the enclosed volume wherein the at least one opening is used to fill the enclosed volume in the fully deflected loop state with biocompatible filling materials for interbody fusion.

According to certain embodiments of the present invention, an implant for motion preservation is disclosed. The implant is deflectable to a deflected loop, for example a fully deflected loop, inside the body, where the loop defines an enclosed volume (or an at least partially enclosed volume, for example if the loop is not a strict loop and has a gap) with the upper and lower surfaces of the body. The implant for interbody fusion further includes at least one opening in one or both of the elongated sides allowing access to the enclosed volume wherein the at least one opening is used to fill the enclosed volume in the fully deflected loop state with inert biocompatible filling materials applicable for motion preservation.

According to certain embodiments of the present invention, an implant system for implanting implants described herein above is disclosed. The implant system includes further an injector containing filling materials such as but not limited to biocompatible materials, bone grafts, bone chips, bone-growth enhancing agents for interbody fusion or inert filling materials, such as cement for interbody fusion or for stabilizing compression fractures, or other nucleus reinforcement or replacement material for motion preservation.

In contrast to prior art implants, which may be straight or circular or of other various shapes, the present implant may be asymmetric, such as D-shaped and may, in a deflected state, comprise an asymmetric loop that may define an at least partially enclosed volume. For example, the implant of the present invention may be comprised of (i) a deflectable piece and (ii) a backbone that is not deflectable or at least not normally deflected. In still further contrast to prior art implants, the deflectable piece may be comprised of a sequence of segments that may be interconnected at effective hinges. In some preferred embodiments, and in contrast to prior art implants, the effective hinges may be lateral cut-outs, for example triangular lateral cut-outs that may close upon deflection. The deflected state, for example the fully deflected state, may be defined by abutment of abutment features (for example surfaces, which may also be called abutment surfaces) of adjacent segments of the sequence. In further contrast to prior art implants, in which the implant opens using a tensioning element or a mechanical linkage, the implant of the present implant may open upon longitudinal pressure applied either to a proximal end of the deflectable piece or to the backbone to generate relative longitudinal movement between at least a distal end of the backbone and the proximal end of the deflectable piece. In contrast to the manner of opening prior art implants, this application of longitudinal pressure may generate relative longitudinal movement between the proximal end of the deflectable piece and at least a distal end of the backbone and may generate an outward horizontal movement (transverse to the longitudinal movement and in a preferred embodiment along a plane of or substantially parallel to an intervertebral disc) of at least a central portion of the deflectable piece away from the backbone, thereby deflecting the deflectable piece to the deflected state to form, with said backbone, an asymmetric loop, such as a D-shaped loop. This may be accomplished in part because in contrast to prior art implants, in which a proximal end of a deflectable portion is either free or interconnected, the implant of the present invention may have a deflectable piece that is free on its proximal end prior to insertion and prior to and during at least a portion of its deflection but meeting (abutting or interconnected to) the backbone at a distal end after the deflection, or at least during the deflection. In further contrast to prior art implants, which may be symmetric and may expand symmetrically after insertion, the implant of the present invention may be asymmetric along an axis defined by a direction of insertion and running between a proximal and distal end of the deflectable piece and situated between the backbone and deflectable piece. Accordingly, the implant of the present invention may expand asymmetrically by deflection of the deflectable piece on only one side of the axis. In further contrast to prior art implants, the height of the backbone may in certain preferred embodiments be at least as great as the deflectable piece (or, in other preferred embodiments, at least as great as a proximal segment of the deflectable piece). In still further contrast to prior art implants, at least one segment may have a curved exterior and/or may have an elliptical and/or anatomically shaped cross-section, at least at a top, bottom and at least one side (i.e. the at least one segment has a cross-section that corresponds to an ellipse at a top, a bottom and at least one side of the at least one segment). Furthermore, in contrast to method of implanting in the prior art, the method of implanting of the present invention may involve inserting the implant laterally, which has clinical benefits, such as avoiding the nerve root, avoiding major blood vessels, eliminating the need for a facetectomy, and allowing very large implants to be implanted to afford greater stability. In further contrast to prior art implantation methods, the method of implanting of the present invention in certain preferred embodiments may involve initially inserting the implant into an anterior portion of a spine and then deployed posteriorly. For example, the implant may be laterally inserted into zone two of the spinal column and then deflected into zone three and/or zone four. In other preferred embodiments, the method of the present invention may involve inserting posteriorly and then deflecting anteriorly. In further contrast to prior art methods, the method of the present invention may involve setting an initial position of the backbone so as to pre-define the final position of the implant. For example, the backbone may be held stationary during deflection of the deflectable piece. In further contrast to prior art methods of implantation, the backbone may be configured to hold at least a majority of the load of the implant and may be configured to be emplaced under or between cortical bone to receive the impact of such load. For example, the backbone may be a solid beam whose width may be at least half the height of the backbone (or in other preferred embodiments, at least two-thirds or at least three-quarters or in some preferred embodiments between one times the height and one and a half times the height or in other preferred embodiments between one half times and one and one half times the height). In still further contrast to prior art implants and methods, one method of the present invention may involve inserting two laterally deflectable implants so that their backbones may be substantially parallel and may be alongside one another and then deflecting each of the implants in opposite lateral directions to define two asymmetric loops. In further contrast to the prior art implantation methods wherein deflection of the implant is lateral or radial, one embodiment of the present invention is a method of implantation involving inserting the implant in a straightened or low curvature state and deflecting vertically to distract an intervertebral space between two discs of a spine. In still further contrast to implantation methods of the prior art, one embodiment of the present invention may involve separately deflecting different sequences of interconnected segments of the deflectable piece of the implant, wherein the different sequences combines comprise the deflectable piece. One application of this is to deflect the implant so as to form a "B" shaped implant. In still further to prior art implant that deflect, the implant of the present invention may utilize a backbone that telescopes to adjust its length and thereby generate the relative longitudinal movement between the proximal end of the deflectable piece and at least a distal end of the backbone.

The principles and operation of an apparatus and method for a laterally deflectable implant according to the present invention may be better understood with reference to the drawings and the accompanying description.

As shown in FIG. 1, a laterally deflectable implant may be in a straightened or low curvature insertion state for insertion into the body. In this case, the implant 10 is in a straightened insertion state. Implant 10 may comprise a deflectable piece 20 that may have a distal end 22 and a proximal end 24 and a backbone 30 that may be configured to meet (i.e. abut or interconnect with) deflectable piece 20, for example at the distal end 22 of deflectable piece 20 (or at the proximal end 24). According to certain embodiments, a deflectable piece 20 may be formed of a single body of flexible material and may have at least a first and a second elongated side.

Backbone 30 is typically generally straight and normally is not configured to deflect.

Backbone 30 may abut or interconnect with deflectable piece at a distal end 36 of backbone 30 (or at a different portion of backbone 30). Typically this positioning may be such that deflectable piece 20 is interconnected with backbone 30 or else deflectable piece 20 may merely abut backbone 30. If the backbone and deflectable piece are abutting without an interconnection, this may still allow application of longitudinal pressure against deflectable piece 20 or backbone 30 to cause relative longitudinal movement of proximal end 24 relative to at least a distal end 36 of backbone 30 causing deflection of deflectable piece 20. "Distal end" of backbone 30 is defined to mean the last 10% of backbone 30. In other preferred embodiments, the relative longitudinal movement of proximal end 24 is relative to at least a "distal part" of the backbone, which may be the last 5%, or in other preferred embodiments the last 15%, or the last quarter, or the last third, or the last 40%, or in still other preferred embodiments the region of attachment of the distal segment to the backbone. In some preferred embodiments, the proximal end 24 of deflectable piece 20 moves longitudinally relative to the entire backbone 30 (particularly when the backbone is not an adjustable length backbone).

Figure 2:
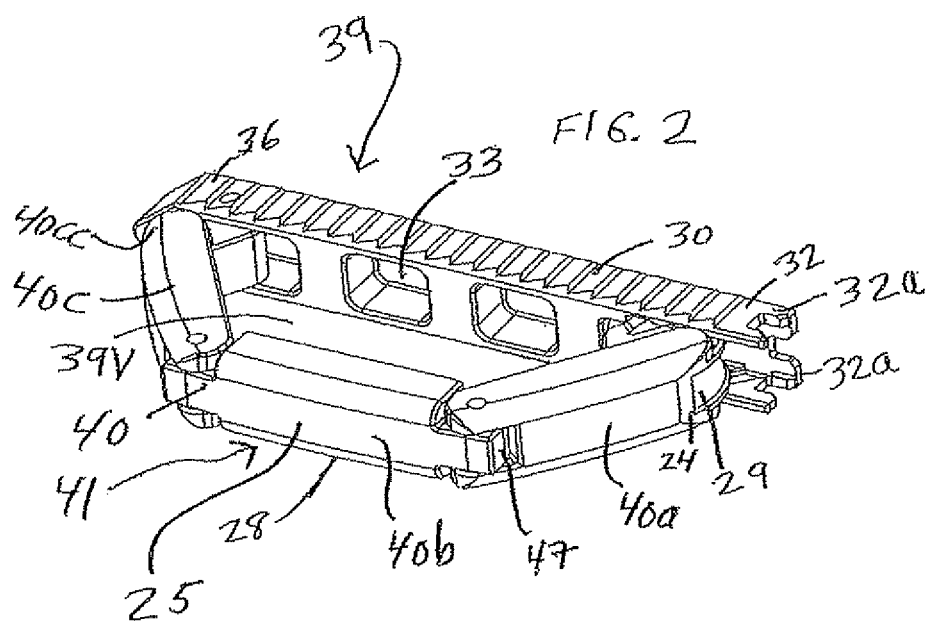
FIG. 2 is an isometric view of the implant of FIG. 1 in a deflected state, in accordance with one embodiment of the present invention.

In some preferred embodiments, deflectable piece 20 and backbone 30 are interconnected even before insertion of the implant 10 into the body. In other preferred embodiments, backbone 30 may be inserted into the body first and then deflectable piece 20 may be inserted so as to interconnect along a rail on backbone 30, for example sliding along the rail longitudinally until deflectable piece 20 abuts a tip 37 of backbone 30. Deflectable piece 20 may be hingedly interconnected with backbone 30 at distal end 22 of the deflectable piece, as shown in FIG. 2. Note that when deflectable piece 30 is in a straightened (or low curvature) configuration, implant 10 is said to also be in a straightened (or low curvature) configuration.

When deflectable piece 20 is in its straightened or low curvature configuration, backbone 30 may extend alongside deflectable piece 20, as shown in FIG. 1. When deflectable piece 20 is in its deflected state, backbone 30 may be alongside only the ends 22, 24 of deflectable piece 20 and backbone 30 may extend from the distal end 22 of the deflectable piece 20 to the proximal end 24 thereof.

As shown in FIG. 2, in addition to abutting or interconnecting with backbone at one end such as a distal end of backbone, deflectable piece 20 in a deflected state, for example after insertion, may also be interconnected (for example hingedly) with said backbone 30 at the proximal end 24 of deflectable piece 20 and backbone 30 may then extend between the distal end 22 and the point of interconnection which may be proximal end 24 of the deflectable piece 20. In some preferred embodiments (not including, for example, embodiments in which the backbone 30 has telescoping portions), the proximal end 24 of deflectable piece 20 is not in contact with the backbone prior to deflection of the deflectable piece 20.

When deflected, for example when fully deflected, the deflectable piece 20 may define, together with backbone 30, an asymmetric loop 39 (or asymmetric modified loop), which may be D-shaped. D-shaped loop 39 may define an at least partially enclosed volume 39V. When the deflectable piece 20 of implant 10 is fully deflected, the asymmetric loop may in some embodiments have a toroidal shape, for example a ring toroid or an oval toroid (or in other embodiments a toroidal polyhedron). The interconnection between proximal end 24 of deflectable piece 20 and backbone 30 may typically occur at or near the completion of the deflection, although this is not a requirement or a limitation of implant 10. In addition, in some preferred embodiments, asymmetric loop 39 may not be fully closed—for example even in a fully deflected state there may be a gap between backbone 30 and the proximal end 24 of deflectable piece 20. Typically, any such gap does not exceed 10% of a length of the backbone (in the case of telescoping backbones, the length of the backbone when the implant is fully deflected) and in other preferred embodiments, does not exceed 15% or 20% or 25% of such length.

Figure 3:
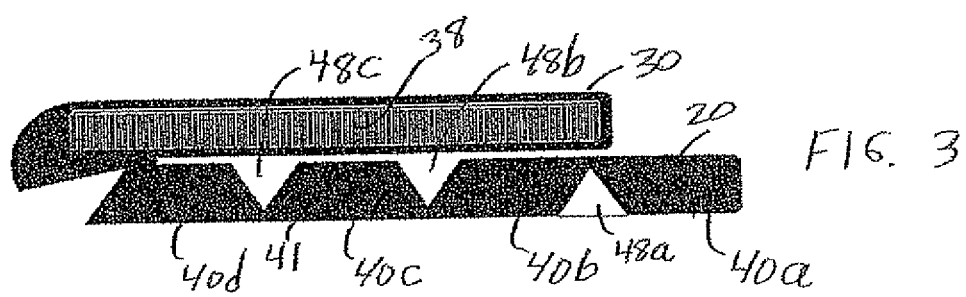
FIG. 3 is a top view of an implant in a straightened configuration for example prior to insertion into a body or after insertion but prior to deflection, in accordance with one embodiment of the present invention.
Figure 4:
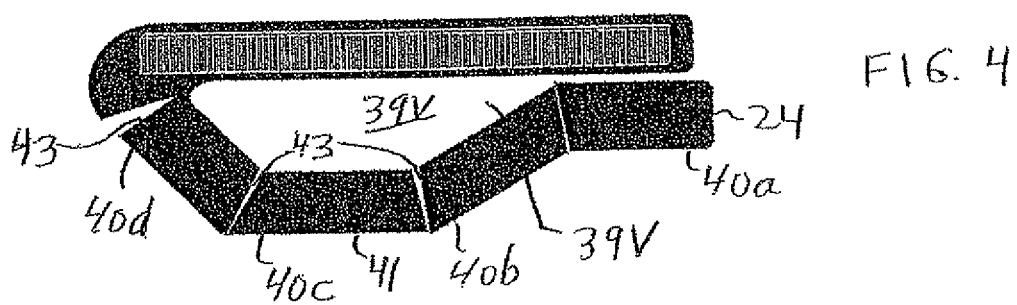
FIG. 4 is a top view of the implant of FIG. 3 in a deflected state, in accordance with one embodiment of the present invention.

As shown in FIG. 2, deflectable piece 20 may comprise a sequence 41 of segments 40, for example segments 40a, 40b and 40c. "Segments 40" is used to refer in general to the segments 40a, 40b, 40c, etc. Segments 40 may be interconnected with one another at effective hinges 47 for example effective hinges 47a, 47b, etc. As shown in FIG. 3, the effective hinges 47 may be comprised of lateral cut-outs 48a, 48b, 48c between segments 40a, 40b, 40c and 40d. The lateral cut-outs 48a-c may be triangular or substantially triangular and as shown in FIG. 4 may close upon deflection. In some preferred embodiments, the sequence 41 of segments 40 is deflectable to a deflected state, for example a fully deflected state, defined at least partially by abutment of abutment features 43 (for example surfaces) of adjacent segments of the sequence 41 of segments 40. The abutment features 43 may function as a limiter feature to prevent rotation about the hinges beyond the desirable range in either clockwise or counterclockwise direction(s). In embodiments without cut-outs, another limiting feature may be used, for example a limiter built-in to the hinge (not shown). In order to improve robustness of the torque of the segments 40, the segments 40 may be interconnected to one another by interdigitation, for example interlocking fingers.

If deflectable piece 20 is comprised of segments 40, then proximal end 24 of deflectable piece 20 is a part of the most proximal segment 40*a*. For clarity, as shown in FIG. 2, middle segment 40*b* may have a side surface 25.

In order for the deflectable piece 20 to change from the straightened or low curvature state shown in FIG. 1 to the deflected state, for example the fully deflected state, shown in FIG. 2, longitudinal pressure may be applied to the proximal end 24 of the deflectable piece 20. As shown in FIGS. 5A-5B, this may be accomplished with a deployer or "pusher" component 60 which may be a separate component or may be located on a holder 50 (FIG. 6). Application of the longitudinal pressure may generate relative longitudinal movement between the proximal end 24 and backbone 30 to cause deflection of deflectable piece 20. In addition, the longitudinal pressure may generate an outward horizontal (lateral) movement (transverse to the longitudinal movement and, in a preferred embodiment, along a plane of or substantially parallel to an intervertebral disc) of at least a portion 28 of the deflectable piece 20 away from the backbone 30, thereby deflecting the deflectable piece 20 to the deflected state to form the asymmetric loop 39 together with backbone 30. The portion 28 referred to may be a central portion of deflectable piece 20, which in this context is not in any way limited to a portion that is right in the middle of deflectable piece 20 or necessarily in a middle segment 40 of the deflectable piece 20. Rather, the central portion is any portion that is not at the very remote end at the distal end 22 and not at the very remote end at the proximal end 24 of deflectable piece 20.

If deflectable piece 20 is not made up of segments, then the central portion 28 may be thought of as a bow expanding outward with the ends fixed. In some embodiments, the outward expansion, i.e. the deflection of the deflectable piece 20, may be centered at a point that is not at the midpoint between the distal and proximal ends 22, 24. The deflection of deflectable piece 20 allows the deflectable piece together with the backbone to form a loop, and in particular a D-shaped loop.

Instead of longitudinal pressure applied against proximal end 24, for example to push proximal end 24, there may be longitudinal pressure applied to backbone 30, for example to pull a distal end 32 of backbone 30. In general, in either case, relative longitudinal movement between backbone 30 and proximal end 24 of deflectable piece 20 may be generated to deflect deflectable piece 20 to its deflected state and thereby form asymmetric loop 39.

Figure 25A:
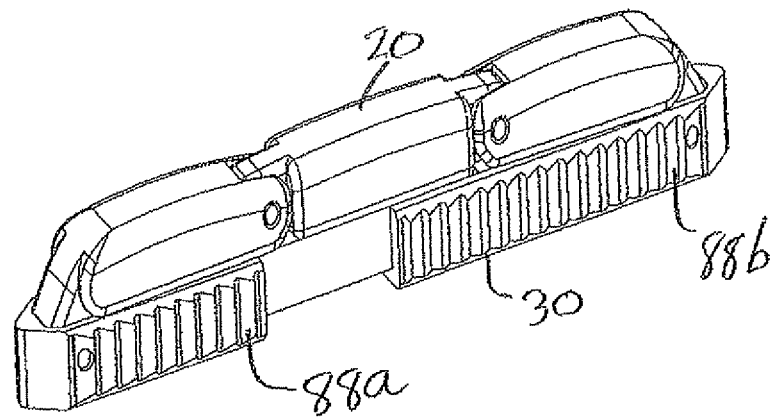
FIG. 25A is an isometric view of an implant with an adjustable length backbone in a straightened state, in accordance with one embodiment of the present invention.
Figure 25B:
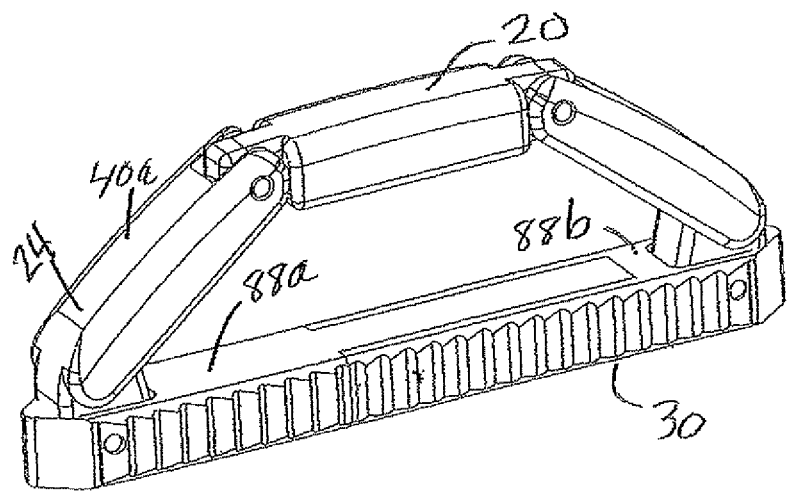
FIG. 25B is an isometric view of an implant with an adjustable length backbone after deflection, in accordance with one embodiment of the present invention.

As shown in FIGS. 25A-25B, backbone 30 may be adjustable in length. Accordingly, in embodiments in which the length of backbone 30 is adjustable and this adjustability is utilized to generate relative longitudinal movement between a proximal end of deflectable piece 20 and at least a distal end of the backbone, the proximal end 24 of deflectable piece 20 may be in contact with backbone 30 (and in fact may be attached to backbone 30) even before deflection of deflectable piece 20. For example, backbone 30 may include a first telescoping portion 88*a* of the backbone 30 that telescopes into or with a second telescoping portion 88*b* of backbone 30. As seen in FIG. 25B, the proximal end 24 of deflectable piece 20 may be attached to first telescoping portion 88*a* of the backbone such that deflection of the deflectable piece 20 is actuated by moving the first telescoping portion 88*a* relative to the second telescoping portion 88*b* of backbone 30. Although the number of telescoping portions in backbone 30 has been described as two, this number can also be greater than two, such as three, four or higher numbers. First and second telescoping portions 88*a*, 88*b* may be linearly aligned (i.e. collinear) as part of backbone 30. Furthermore, in a preferred embodiment, when first and second telescoping portions 88*a*, 88*b* telescope within one another, they do so without one telescoping portion sticking out the other longitudinal end of the other telescoping portion. In preferred embodiments, first and second telescoping portions maintain substantially equal heights even when telescoping within one another (since for example the outer surfaces of each may not participate in the telescoping).

In FIGS. 24A-E, the deflectable piece 20 is comprised of a first sequence of segments associated with first and second telescoping portions 88*a*, 88*b* of the backbone 30 and is comprised of a second sequence 41 of segments associated with third and fourth telescoping portions 88*a*, 88*b* of the backbone.

As shown by FIGS. 27A-K, the present invention may utilize in any suitable embodiment of implant 10 (or method or assembly) an implant 10 having an adjustable-in-length backbone 30 in which axial movement between parts of the backbone 30 is accompanied by relative rotation of the parts. The backbone may comprise a rotatable element 93 and an annular element 95, the rotatable element attached to or abutting the deflectable piece and configured to move longitudinally by rotatingly engaging the annular element. Rotatable element 93 may be a tube 93 such as a threaded tube 93 that is threaded at a distal portion 93*a* thereof, such as at a tip 93*a*. The annular element 95 may be a threaded nut 95, such as a female threaded nut, that receives the rotational movement of the threaded tube. Threaded nut 95 may be fixed. This embodiment resembles telescoping but differs from "telescoping" (which typically involves axial movement of a part within a part without accompanying rotation of these parts) since here, besides longitudinal/axial movement of a part of backbone 30 within another part, there may also be rotation of at least one part of the backbone 30, and typically rotational engagement or relative rotation between that one part and at least one other part of the backbone 30.

Figure 27A:
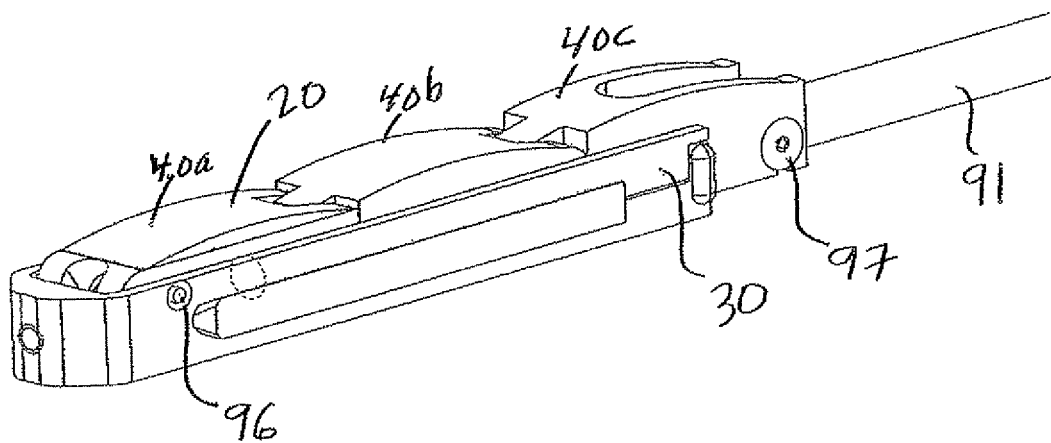
FIG. 27A is an isometric view of an implant, deployment tube and holder shaft, in a straight configuration before deflection, in accordance with one embodiment of the present invention.
Figure 27B:
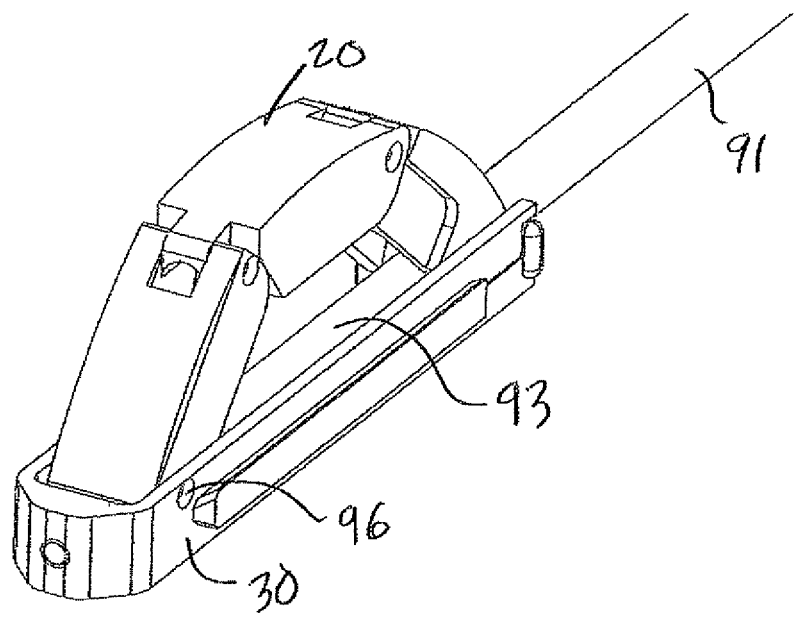
FIG. 27B is an isometric view of the implant, deployment tube and holder shaft of FIG. 27A after deflection, in accordance with one embodiment of the present invention.
Figure 27C:
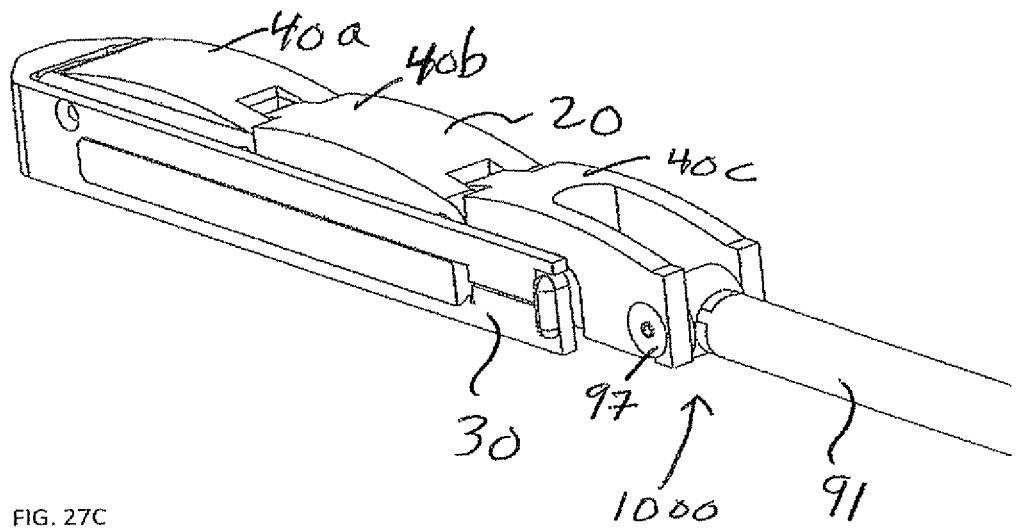
FIG. 27C is an isometric view of the implant, detachment tube and holder shaft of FIG. 27A shown from an opposite side and before deflection, in accordance with one embodiment of the present invention.
Figure 27D:
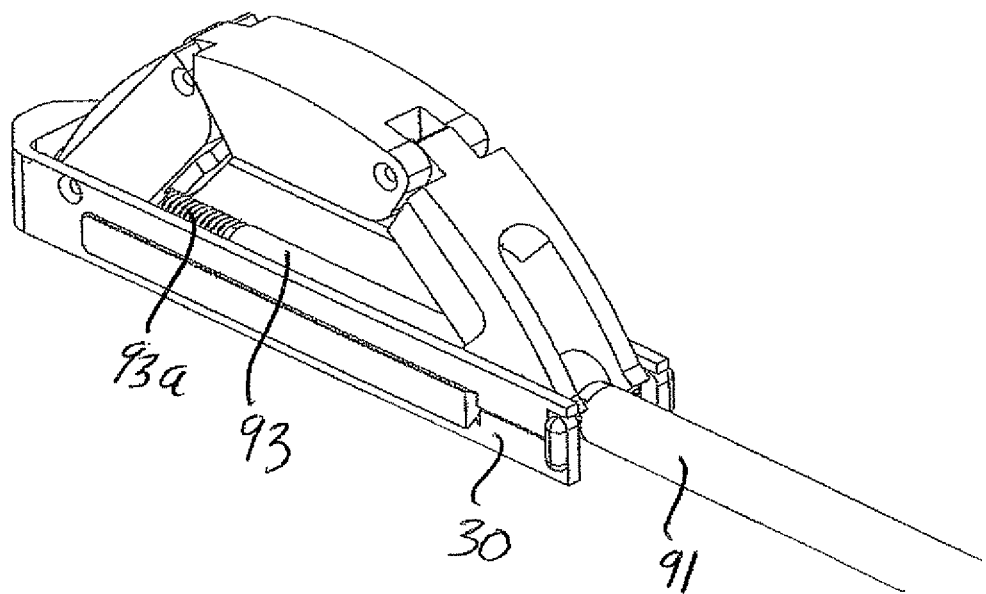
FIG. 27D is an isometric view of the implant, deployment tube and holder shaft of FIG. 27C after deflection, in accordance with one embodiment of the present invention

As shown in FIG. 27A, a pin 96 may be used to connect a segment 40*a* (which in the view of FIG. 27A is a distal segment) of deflectable piece 20 to backbone 30. Furthermore, a proximal axis/axle 97 may be used to attach a proximal end of rotatable element 93 to deflectable piece 20, for example to proximal segment 40*c*, or in general to a proximal part of deflectable piece 20. Since the rotatable element is attached to (or abutting) the proximal part of the deflectable piece, the deflectable piece may move longitudinally relative to at least a distal end of the backbone when the rotatable piece 93 advances longitudinally with respect to annular element 95.

An implant assembly 1000 (FIG. 27C) may include an implant 10 with this kind of adjustable-in-length backbone 30 and may further include a holder shaft 92 running through the backbone 30, the holder shaft 92 including a holder shaft tail 92*a* jutting out a proximal end of the implant. Such an assembly may further comprise a deployment tube 91 enclosing the holder shaft tail 92*a* and being operatively engaged to the rotatable element 93 to rotate the rotatable element 93.

Figure 27E:
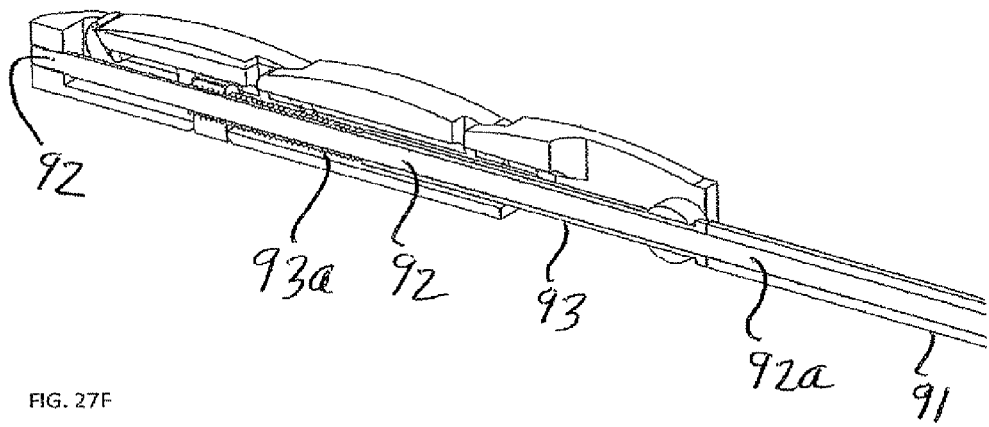
FIG. 27E is a vertical sectional view of the implant, deployment tube and holder shaft of FIG. 27C with the implant in straightened configuration, in accordance with one embodiment of the present invention.
Figure 27F:
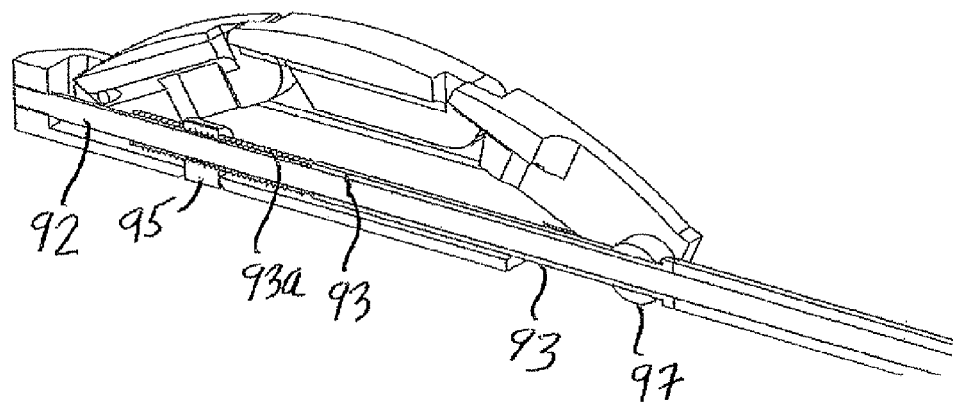
FIG. 27F is a vertical sectional view of the implant, deployment tube and holder shaft of FIG. 27C with the implant in partially deflected state, in accordance with one embodiment of the present invention.
Figure 27G:
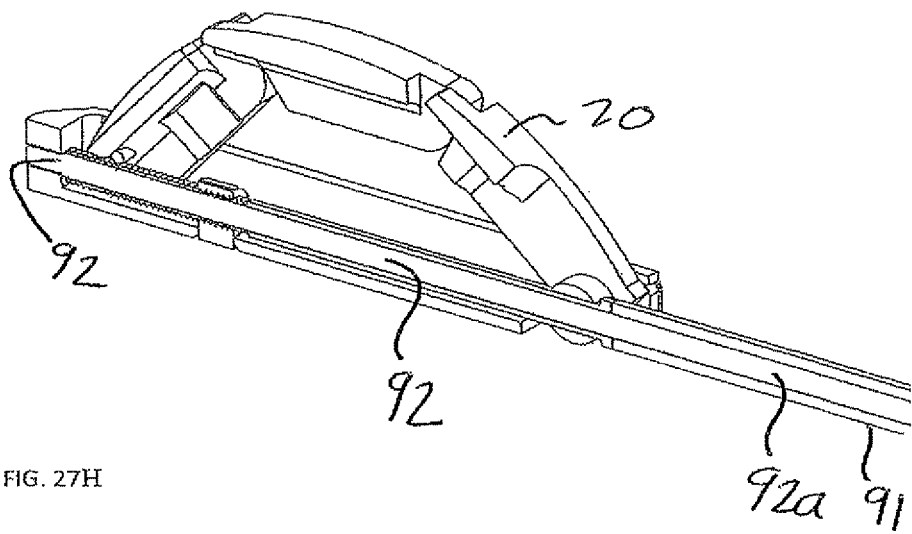
FIG. 27G is a vertical sectional view of the implant, deployment tube and holder shaft of FIG. 27C with the implant in partially deflected state, in accordance with one embodiment of the present invention.
Figure 27H:
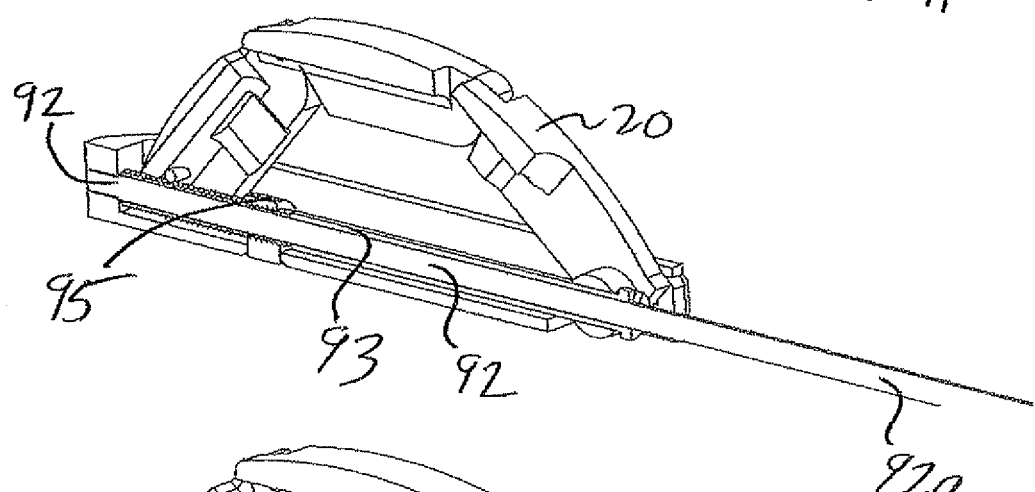
FIG. 27H is a vertical sectional view similar to FIG. 27G except with the deployment tube detached, in accordance with one embodiment of the present invention.
Figure 27I:
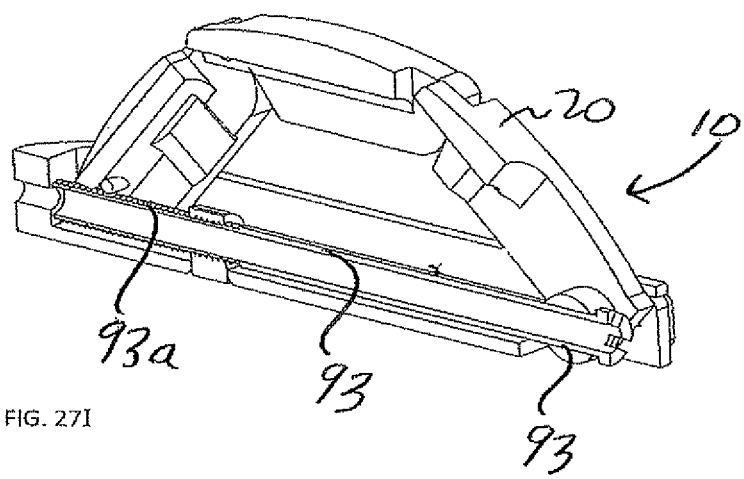
FIG. 27I is a vertical sectional view similar to FIG. 27G except with the deployment tube detached and the holder shaft also removed, in accordance with one embodiment of the present invention.
Figure 27J:
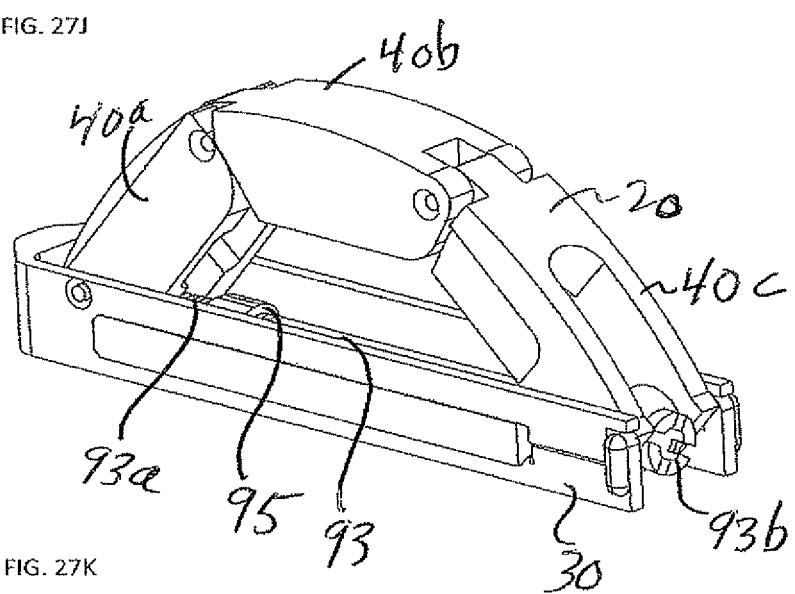
FIG. 27J is an isometric view of the deflected implant without the deployment tube or holder shaft and revealing the engagement teeth at the rear of the threaded tube.
Figure 27K:
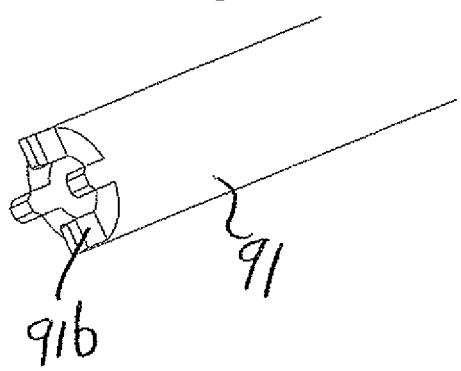
FIG. 27K is an isometric view of the end of a disconnected deployment tube showing its engagement teeth, in accordance with one embodiment of the present invention.

FIG. 27E is a vertical sectional view of an implant 10 whose deflectable piece 20 comprises segments 40*a*, 40*b*, 40*c* and whose backbone comprises a threaded tube 93 and a female threaded nut 95. In practice, a user may first insert a holder shaft 92 through implant 10, for example through the entire length of implant 10. The holder shaft 92 may connect to a distal tip of implant 10. The holder shaft 92 may have a holder shaft tail 92*a* that sticks out the proximal end of implant 10 and may attach to a handle (see FIGS. 5A-6). The user may then attach a deployment tube 91 over holder shaft tail 92a such that engagement teeth 91b of the deployment tube 91 mate with engagement teeth 93b at the proximal end of threaded tube 93, as seen in. FIGS. 27G-27K, especially FIGS. 27J-27K.

It should be understood that the embodiments in which the length of the backbone 30 is adjustable may have any of the other structural features of implant 10 described herein, and may be used in any of the methods described below, although as indicated such embodiments typically would not employ a deflectable piece 20 whose proximal end 24 is not in contact with the backbone 30 of the implant prior to deflection.

Furthermore, in this patent application in general, the structural features and method steps described in the context of one embodiment, or illustrated in a drawing of one embodiment, are not limited to that embodiment and may be adapted to any of the implants, methods, assemblies or systems described herein, unless otherwise indicated.

Asymmetric loop 39 may assume other shapes besides a D-shape such as rectangular, trapezoidal, triangular and B-shaped (i.e. two D-shaped implants with backbones that are substantially aligned). Moreover, in certain preferred embodiments, there may be two implants lined up such that the backbones 30 of each implant are substantially parallel or alongside one another such that the two implants together form two D-shapes. Moreover, "D-shape" does not require a perfect D. There could be a slight projection of backbone 30 beyond where backbone 30 meets deflectable piece 20 on the proximal and/or distal end.

As seen from FIG. 1, proximal end 24 of deflectable piece 20 may be a free proximal end during insertion of the implant, i.e. not connected to backbone 30 or to another element of implant or of holder 50 or deployer 60. Proximal end 24 may be free proximal end during at least a majority of the deflection of the deflectable piece, the majority measured by reference to how great of an outward horizontal distance the deflectable piece 20 has moved. In some preferred embodiments, proximal end 24 is attached to backbone 30 at or near the end of the application of longitudinal pressure by deployer 60. Accordingly, proximal end 24 may be free other than in the deflected state, for example the fully deflected state, of the deflectable piece 20. In other preferred embodiments, however, proximal end 24 may be free even in the fully deflected state. In some preferred embodiments, for example as shown in FIG. 1, the proximal end 24 of deflectable piece 20 is not in contact with backbone 30 prior to deflection of deflectable piece 20.

Figure 7A:
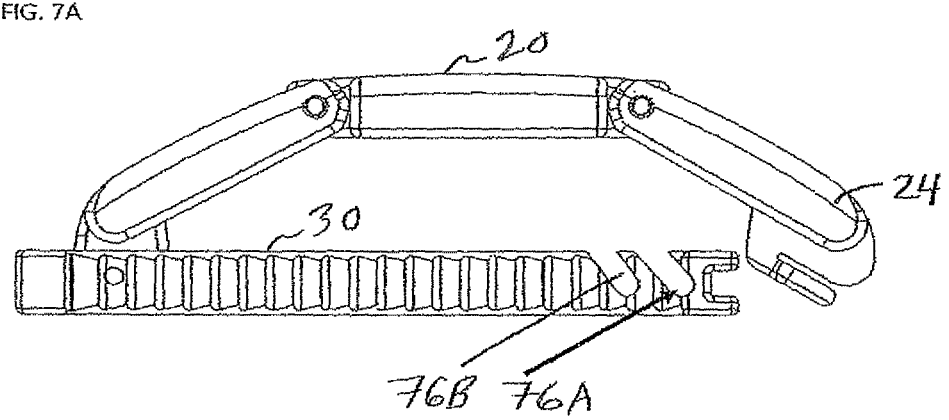
FIG. 7A is a top view of an implant showing a locking mechanism, in accordance with one embodiment of the present invention.
Figure 7B:
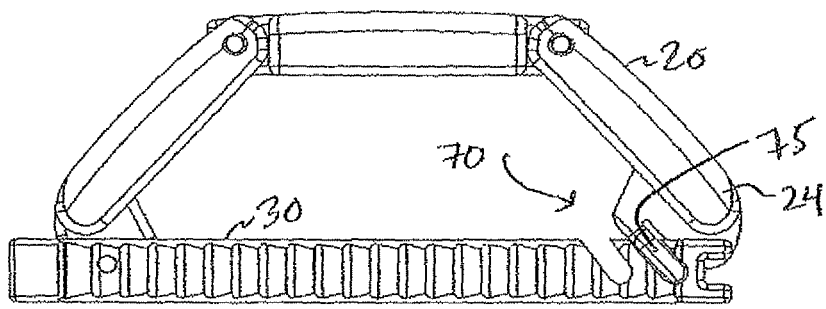
FIG. 7B is a top view as in FIG. 7A with a tooth in a slot in locked position, in accordance with one embodiment of the present invention.

As shown in FIG. 2 and FIG. 7B, in some preferred embodiments, a proximal end 24 of deflectable piece 20 may interconnect with the backbone at a proximal end of backbone 30, for example at the culmination of the deflection of deflectable piece 20. Typically, backbone 30 is not configured to deflect and is normally rigid. Nonetheless, in order to facilitate locking or other engagement to deflectable piece 20, backbone 30 could for example have a slit allowing at least a portion of backbone 30 to bend, for example up to 15 or 20 rotational degrees of the longitudinal axis of backbone 30 (as measured from a distal to a proximal end of backbone 30), so as to facilitate engagement of a proximal end of deflectable piece 20 to backbone 30, for example at the culmination of the deflection of deflectable piece 20. In this version, backbone 30 would resume its original shape after the engagement with deflectable piece 20.

As can be seen from FIGS. 1-2, since backbone 30 and deflectable piece 20 are not identical, implant 10 may be asymmetric about a longitudinal axis running from one end of deflectable piece 20 to the other (for example in a direction of insertion of the implant 10) when the implant 10 is in a deflected state. The asymmetry may be particularly pronounced for example when the longitudinal axis is situated between the deflectable piece 20 and the backbone 30, for example where the backbone, deflectable piece and longitudinal axis are all on substantially one plane. The implant (and the loop) in a deflected state may be asymmetric such that the implant (and the loop) does not have an axis of symmetry parallel to the backbone 30.

The implant 10, including the backbone 30 and deflectable piece 20, may be made of any suitable biocompatible material (i.e. titanium, PEEK, shape memory alloy, steel, cobalt-chrome alloy etc.). The cross-section of implant 10 may be straight, as shown in FIGS. 1-2, or may be angled to create a lordotic angle between the vertebral bodies. Optionally, the lordotic angle may be created by having segments (of deflectable piece 20) of varying or graduated heights within the same implant 10.

An end 32 (FIG. 2) of backbone 30 (for example proximal end 32) may interface with a holder instrument 50 (see FIG. 6 and FIG. 12) that holds implant 10. As seen from FIG. 6, holder 50 may be an elongated instrument and may be made of metals, polymers or a combination of materials. One end 52 (i.e. a distal end) of holder 50 may have one or more such interfaces with functions such as anti-rotation of implant device 10 on the instrument 50, quick connect/quick release or other attachment/release method of the implant 10. For example, the anti-rotation feature 32a on the proximal end 32 of backbone 32 may interface with an anti-rotation feature on the distal end of holder 50. There may be separate features for attachment and release of implant 10 from the holder instrument 50. There may be a feature designed to minimize user error in attaching implant device 10 to the holder 50. The interface features may appear on corresponding ends of the holder 50 and backbone 30. The proximal end 54 of holder 50 may have a surface for pushing or tapping to effectuate advancing the implant 10 into the desired location in the body. The interface on distal end 52 may be connected to a component(s) 66 (i.e. a knob, button, dial, handle, etc.) on the proximal end 54 so that the user can perform the necessary functions to the implant 10 (connect, deploy, disconnect, etc.).

Figure 5:
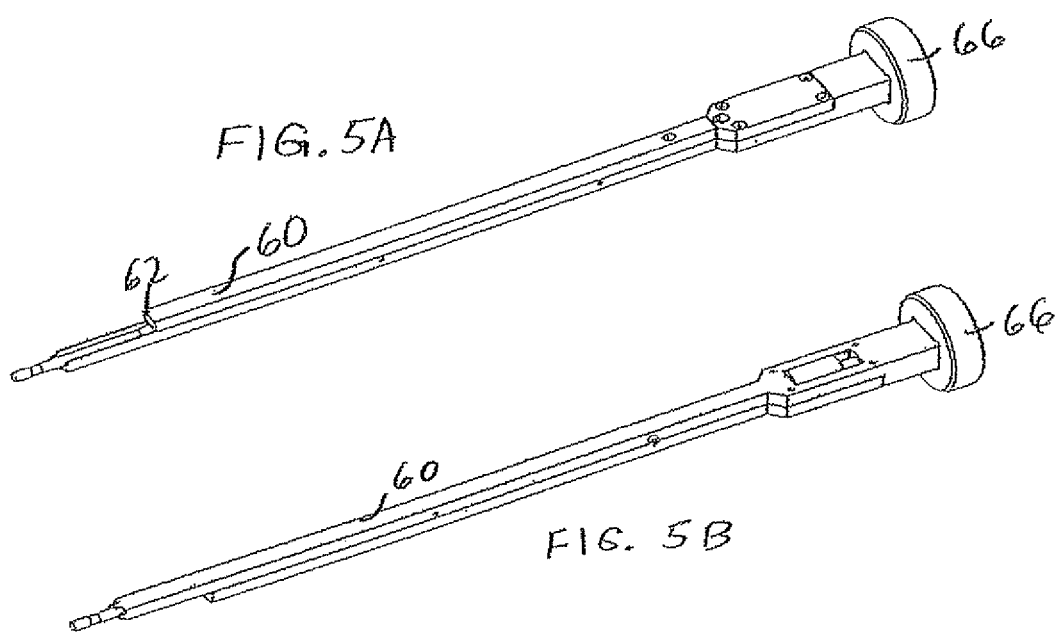
FIG. 5A is an isometric view from the top of a deployer on a holder, in accordance with one embodiment of the present invention.
FIG. 5B is an isometric view from the bottom of a deployer on a holder, in accordance with one embodiment of the present invention.
Figure 6:
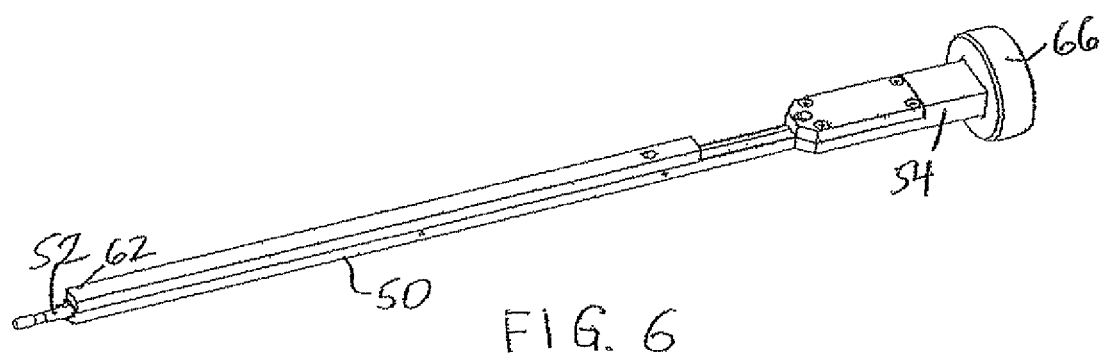
FIG. 6 is an isometric view of a holder, in accordance with one embodiment of the present invention.

As shown in FIG. 5A, deployer 60 may have a component for aligning or directing a biocompatible material such as bone into the window 29 of deflectable piece 20 or of a segment(s) of the sequence 41 of segments 40. Deployer 60 may be integrally formed as part of the holder 50 and located on holder 50 or may be a separate instrument, or in a third possibility, deployer 60 may be attached to holder 50 intraoperatively. Deployer 60 may have a distal end 62 that interfaces with a proximal portion of deflectable piece 20, in particular in certain preferred embodiments with a segment of implant 10, most likely proximal end 24 forming part of proximal segment 40a of implant 10. When the deployer 60 is advanced longitudinally, deployer 60 pushes or moves the proximal end 24, this causes deflection of the deflectable piece 20 to the deflected state. As seen from FIG. 5A, deployer 60 may be advanced axially by squeezing or pushing handles 66 located on the holder and deployer 60. The handles may be fixed on the holder 50 and deployer 60 or may be removable. The handle 66 may have a spring component (not shown) to return the handles 66 to their original position after squeezing/pushing them to advance the deployer 60. The holder 50 and/or deployer 60 described in FIGS. 5A-6 may be utilized with any suitable implant or method or assembly or system described in this patent application, although for embodiments in which the backbone 30 is telescoping, the deployer 60 would more typically interact directly with backbone 30 rather than directly with deflectable piece 20 (although even in this telescoping backbone embodiment a deployer 60 could instead interact directly with deflectable piece 20). Furthermore, the adjustable in length backbone embodiment shown in FIGS. 27A-K may utilize its own suitable holder shaft 92 and deployment tube 91, as described therein, and the deployment tube 91 used for this embodiment may interact directly with the backbone or backbone element (i.e. threaded tube 93), as described.

In certain preferred embodiments, the implant 10 in its final position may protrude beyond the vertebrae on the ipsi (proximal to the holder/deployer) and/or contra lateral side.

Figure 8:
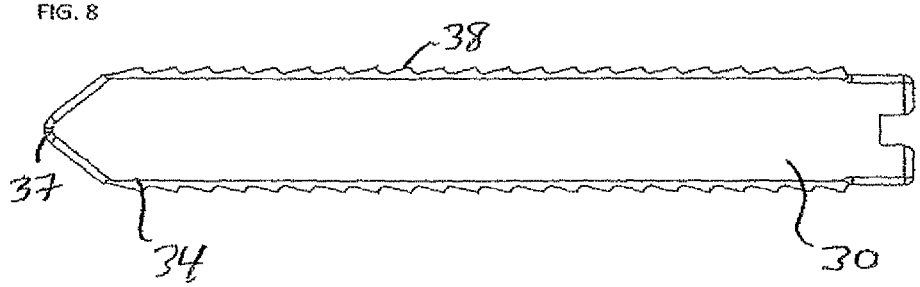
FIG. 8 is a front view of a straight beam used as a backbone for an implant and having anchoring ridges on a top and bottom surface, in accordance with one embodiment of the present invention.

As shown in FIGS. 1-2, the height of backbone 30 may be at least as great as the maximum height of the deflectable piece 20. Typically, backbone 30 may be elongated. Backbone 30 may be a beam, such as a solid beam or a beam that is mostly solid, or solid except for particular openings. "Solid" does not preclude being solid with openings. A "beam" is defined to have two dimensions other than its length such that an average size of one of those two dimensions is at least 30% of an average size of the second of those two dimensions of the beam. As shown in FIG. 8, for example, a straight beam used as backbone 30 may have anchoring ridges 38 on a top surface 31 and on a bottom surface 34. This beam may be used in motion preservation implants of the present invention. The top 31 of the beam 30 (i.e. the backbone 30) may be configured to engage cortical bone in the body and receive an impact from a load of the cortical bone.

Deflectable piece 20 may have a height, a width and a length. The length of deflectable piece 20 may be along a direction of insertion of the implant and may be by far the largest dimension. In some preferred embodiments, backbone 30 may be configured such that the width of the backbone (the dimension transverse to the height and transverse to the length) is at least half as large as a height of the backbone, or in other preferred embodiments at least three-quarters as large as the height, or between one half and one and a half the height in other preferred embodiments. The "height" of the backbone 30 is defined to mean the dimension perpendicular to the plane in which the implant 10 device opens. The "width" of the backbone 30 is the dimension transverse to the elongated length of the implant (and is parallel to the axis referenced herein that runs from the proximal and distal ends of the deflectable piece and is situated between the backbone and the deflectable piece). The width of backbone 30 allows it to withstand a load. Although in general backbone 30 may be hollow, solid or partially hollow, in preferred embodiments, backbone 30 may be configured to hold at least a majority (or in some other preferred embodiments at least two-thirds or at least three-quarters) of a load held by the implant 10. Implant 10 may be placed under cortical bone (for example the bone of a spinal disc adjacent a vertebral body) and the top surface 31 of the beam may be configured to engage cortical bone in the body and receive an impact from a load of the cortical bone. Implant 10 may be anatomically shaped to similarly match the contour of the vertebral endplate.

In motion preservation implants 10, the brunt of the necessary impact to cross the annulus to the contralateral side may be carried by the straight beam. The beam 30 may take its seat on the annular ring after proper sizing is performed. Stability of the implant relies on the initial small aperture in the annulus to allow passage of the implant—and then the gradual sinking of the ridges 38 along the beam 30 into the surrounding tissues. The beam is the most anteriorly located part of the implant 10, mechanically supporting the lordosing effect. Accordingly, the height of the beam may be greater than the height of the deflectable piece.

As shown in FIGS. 1-2, backbone 30 may have a window 33 or an opening to allow biocompatible material (such bone graft) to pass into the anterior area of the vertebral body, i.e. zone one. Backbone 30 may also have a contoured tip 37 (FIG. 1), for example in the form of a bullet nose, to ease insertion of the implant device 10 in between hard tissue (i.e. two adjacent vertebral bodies). Backbone 30 may also have ridges 38, as shown in FIGS. 3-4 on a surface (for example top surface 31 or a bottom surface or side surface) that comes into contact with the tissue of the body in order to prevent movement in an undesired direction. Ridges 38 may be in the form of teeth, pyramids, knurls or similar structures. Ridges 38 may be perpendicular to a length of the backbone, as shown in FIGS. 3-4, or the ridges 38 may be parallel to such length, at an angle, in a combination of directions, and may be on all or only part of the surface. Furthermore, the ridges 38 may vary in height or may be of the same height, and ridges 38 may be straight or curved.

In a preferred embodiment, there is at least one opening 29 (FIG. 2) in the sequence 41 of segments 40 to allow access to the at least partially enclosed volume in the loop for insertion of biocompatible material such as bone graft. In a preferred embodiment, the opening 29 is in a proximal segment 40a or in another segment 40. In other embodiments, opening 29 can be between adjacent segments 40.

Proximal segment 40a (or in embodiments without segments, proximal end 24) may have an interface with pusher component 60 (FIGS. 5A-5B) which allows the segments 40 to be pushed and advanced from the straight configuration to the deflected or fully deflected state.

In some preferred embodiments, deflectable piece 20, which may be comprised of the sequence 41 of segments 40, is resiliently biased towards the fully deflected state, and is temporarily deformed to the insertion state. In this case, a guide may maintain deflectable piece 20 straight during insertion and removal of the guide then permits deflection of the deflectable piece 20, for example by deflection of segments 40, to an original shape. In this sense, the deflectable piece 20 exhibits elastic memory.

Figure 9:
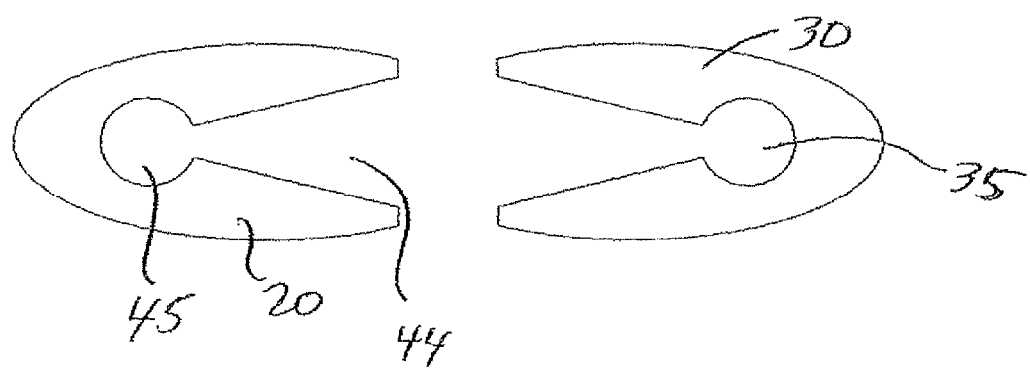
FIG. 9 is an end view of an implant including a backbone and a deflectable piece, in accordance with one embodiment of the present invention.
Figure 10:
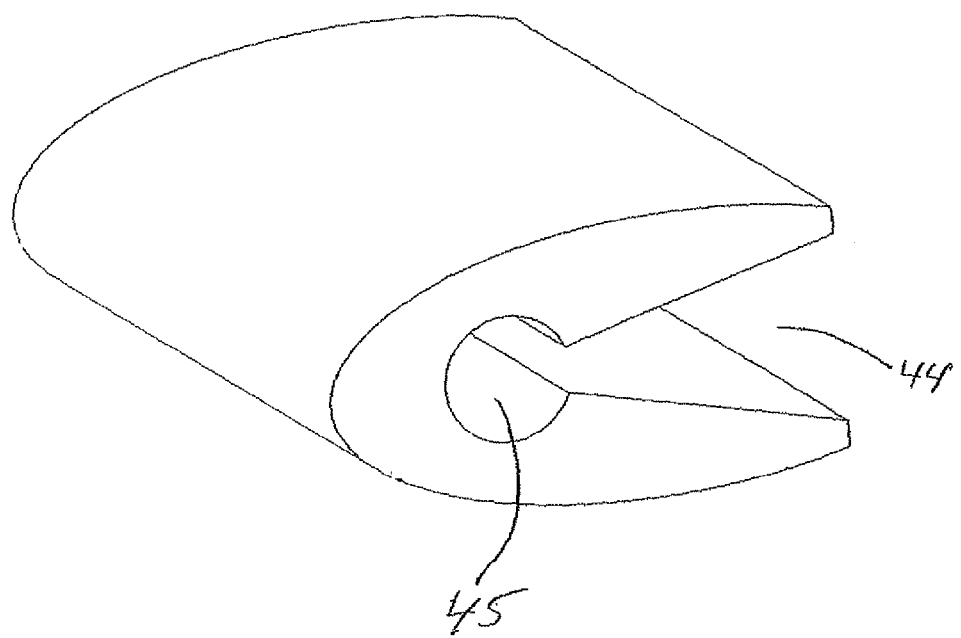
FIG. 10 is an isometric view of a segment of a deflectable piece showing a curved exterior, in accordance with one embodiment of the present invention.

As shown in FIGS. 9-10, which is an end view of the backbone 30 and deflectable piece 20, a hollow 45 (i.e. a cavity 45) of at least one segment 40 of the sequence 41 may be cut out to allow axial flexibility of the implant 10 in response to the repeated impacts of axial loading. The term "axial loading" as used herein means loading in the height direction (i.e. perpendicular to the plane in which the implant 10 opens). Backbone 30 may also have a hollow cut-out 35, as shown in FIG. 9. As also shown in FIGS. 9-10, at least one segment of the sequence may also have a lateral cut-out 44 extending to the hollow 45. At least one segment 40 (and in some preferred embodiments all segments or all except one segment) may have a curved exterior. As shown in FIGS. 9-10, the at least one segment may have an elliptical cross-section at a top, a bottom and at least one side of the at least one segment, that is the at least one segment may have a cross-section that corresponds to an ellipse at a top, a bottom and at least one side of the at least one segment. This may be useful for flexibility for axial loading in the case of motion preservation implants. In addition, deflectable piece 20, and in particular segments 40, may have curved edges to form a bullet nose shape (i.e. similar to such a shape in backbone 30) in order to ease the deployment of the device 10 in-between hard tissue (for example two adjacent vertebral bodies) in the body. As with the other structural features described herein, the hollow cut-out, lateral cut-out, curved exterior and other structural features shown in FIGS. 8-10 may be applied to the deflectable piece 20 (segmented or non-segmented) and backbone 20 (whether or not adjustable in length) of any suitable implant, method step, assembly or system described in this patent application. In addition, although the drawings herein for the most part illustrate implants with a segmented deflectable piece in the various embodiments herein, the deflectable piece 20 may be a flexible non-segmented piece, as described herein.

Figure 12:
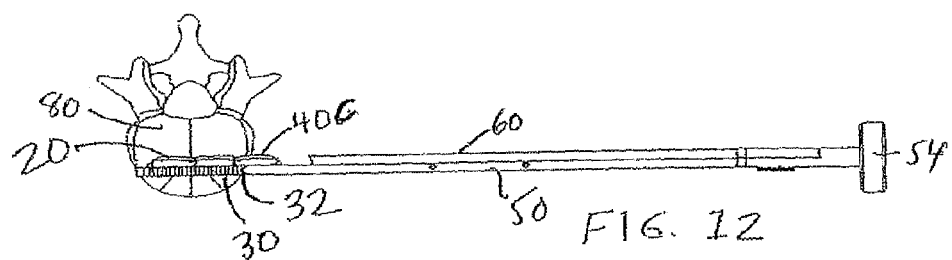
FIG. 12 is a top view of an implant positioned over zone two of a vertebral body by lateral access, the implant in a straightened configuration and held by a holder; in accordance with one embodiment of the present invention.
Figure 13:
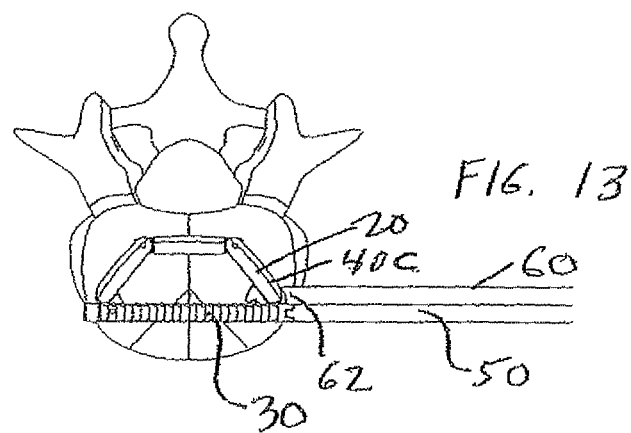
FIG. 13 is a top view of the implant of FIG. 12 wherein the implant backbone is positioned over zone two of the vertebral body but the deflectable piece has been deflected into zone three by the deployer on the holder, in accordance with one embodiment of the present invention.
Figure 14:
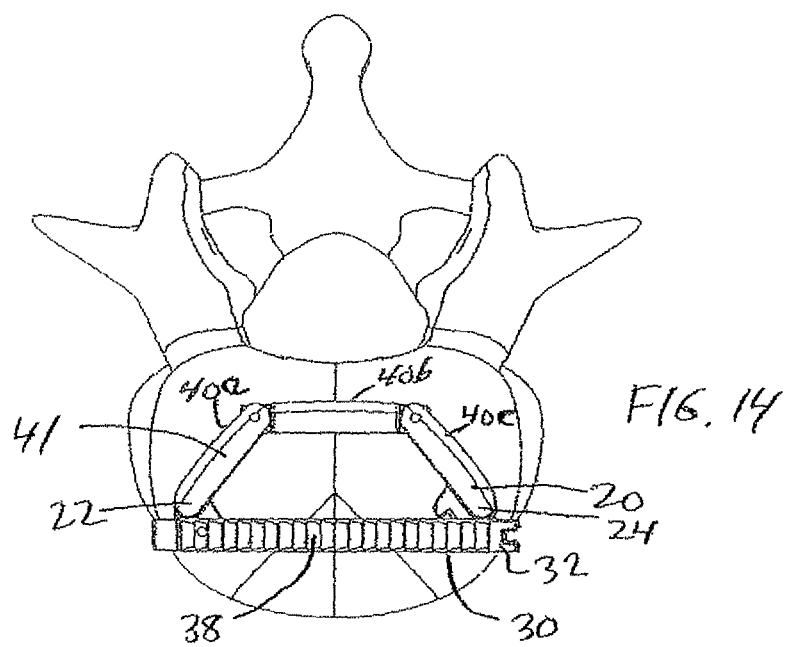
FIG. 14 is a top view of an implant positioned on the vertebral body as in FIG. 13, but with the holder and deployer having already been separated and removed from the implant, in accordance with one embodiment of the present invention.
Figure 21:
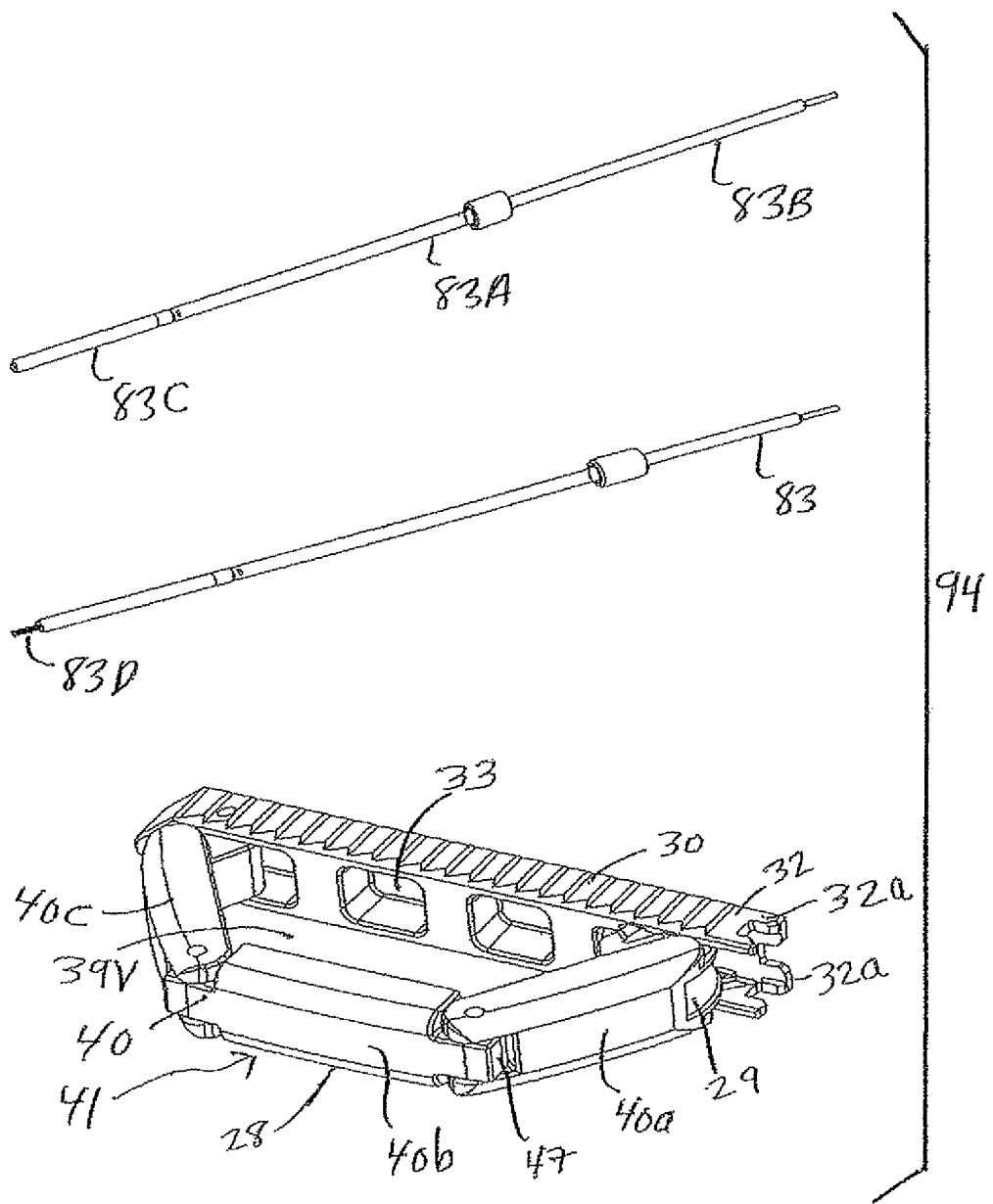
FIG. 21 shows isometric views of an implant and a biocompatible-material-delivery device, in accordance with one embodiment of a system of the present invention.

As shown in FIGS. 12-13, the present invention may also be described as an implant system comprising the implant 10 and further comprising an elongated conduit for inserting said implant in said straightened insertion state into the body. A shown in FIG. 21, the present invention may also be described as a system 94 comprising the implant 10 and further comprising a delivery device such as an injector 83 containing filling material selected from the group consisting of: biocompatible materials, bone grafts, bone chips, bone-growth enhancing agents for interbody fusion, cement and filling materials, for motion preservation. Injector 83 may include a body 83A, a plunger 83B and a cartridge 83C. As shown in the lower depiction of the delivery device 83, injector may also include a tip 83D that passes through body 83A and cartridge 83C. Cartridge 83C may be a tube with one end to fit the window 29 of implant 10 and the other end to attach to the remainder of device 83. Plunger 83B may interface or connect with implant holder 50 (FIG. 6 and FIG. 12) and other delivery instruments. After the cartridge 83C is filled with the biocompatible material such as bone graft, cartridge 83C may be attached to the body 83A of delivery device 83 at a time when the plunger 83B is in the "back" position. The device is then positioned so that the distal tip of the cartridge 83C is placed at the delivery window 29 of implant 10. The plunger 83B is then advanced so that it pushes the biocompatible material through cartridge 83C and into the implant 10. The device 83 may then be removed. If additional biocompatible material is needed, such material may be inserted into cartridge 83C and the remaining steps repeated as necessary.

Figure 7C:
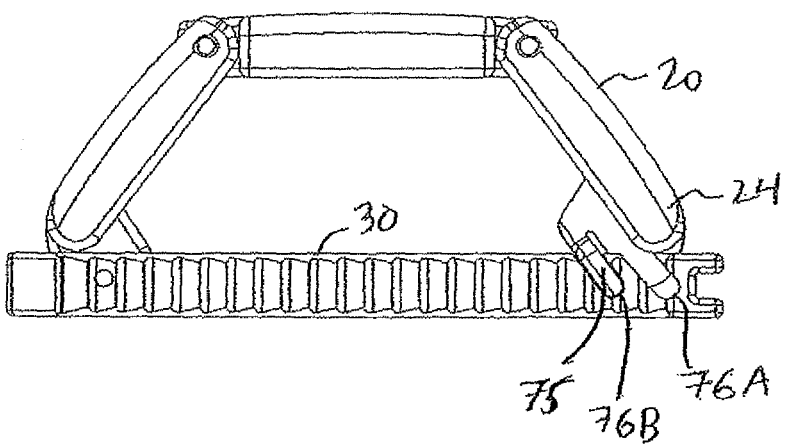
FIG. 7C is a top view as in FIG. 7A with a tooth locked in a second locking position, in accordance with one embodiment of the present invention.

As shown in FIGS. 7A-7C, implant 10 may also comprise a locking arrangement to retain said implant in the pre-defined deflected state or range and/or to prevent undesired motion between backbone 30 and deflectable piece 20 (or at least one segment 40 of deflectable piece 20). The locking arrangement may include at least one element selected from: cords, cables, strips, hooks, ratchets, interconnections and snaps. Locking mechanism 70 may be on segments 40. For example, as shown in FIG. 7A, backbone 30 has slots 76A, 76B or other female elements into which a one or more teeth 75 (FIG. 7B) mate. Teeth 75 may project from a segment 40, for example on an internal side of segment 40. FIG. 7C depicts teeth 75 positioned in an optional second locking position by mating with a second slot 76b on backbone 30. Although the locking mechanism 70 illustrated in FIGS. 7A-7C has been described in the context of the specific implant shown in these figures, it should be emphasized that, as with other structural features described herein, this locking mechanism 70 or another locking arrangement described herein may be utilized on any suitable implant or assembly or system or method step outlined in this patent application.

Optionally, there may be locking mechanisms between segments to provide segmental interlocking. In embodiments where deflectable piece 20 is not comprised of separate segments, but rather is comprised of a single flexible piece of material, deflectable piece 20 may deflect by deforming reversibly.

Figure 15:
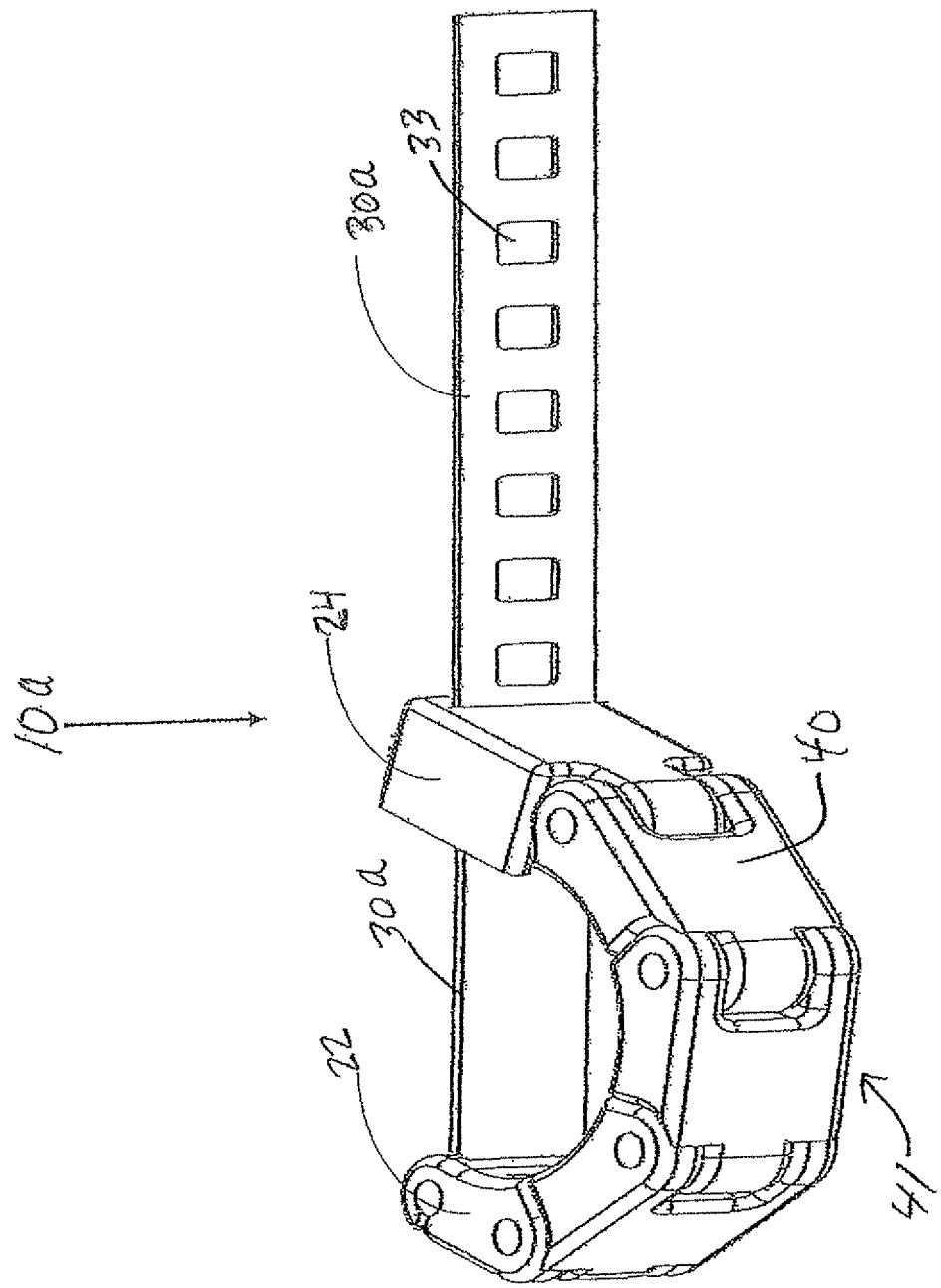
FIG. 15 is an isometric view of an implant with a deflected sequence of segments in the deflectable piece wherein the backbone is flat.

As shown in FIG. 15, in certain other embodiments, implant 10a may utilize a backbone 30a that may comprise a flat and relatively thin segment that may be hingedly interconnected with the sequence of segments of the deflectable piece 30 at a distal end of said sequence. In this case, the sequence 41 of segments may be configured to slidingly interconnect with said flat segment 30a at a proximal end 41a of the sequence of segments 40. FIG. 15 shows the deflectable piece 20 after longitudinal pressure has been applied to generate a sliding longitudinal movement of the sequence 41 relative to the backbone 30a.

Figure 11:
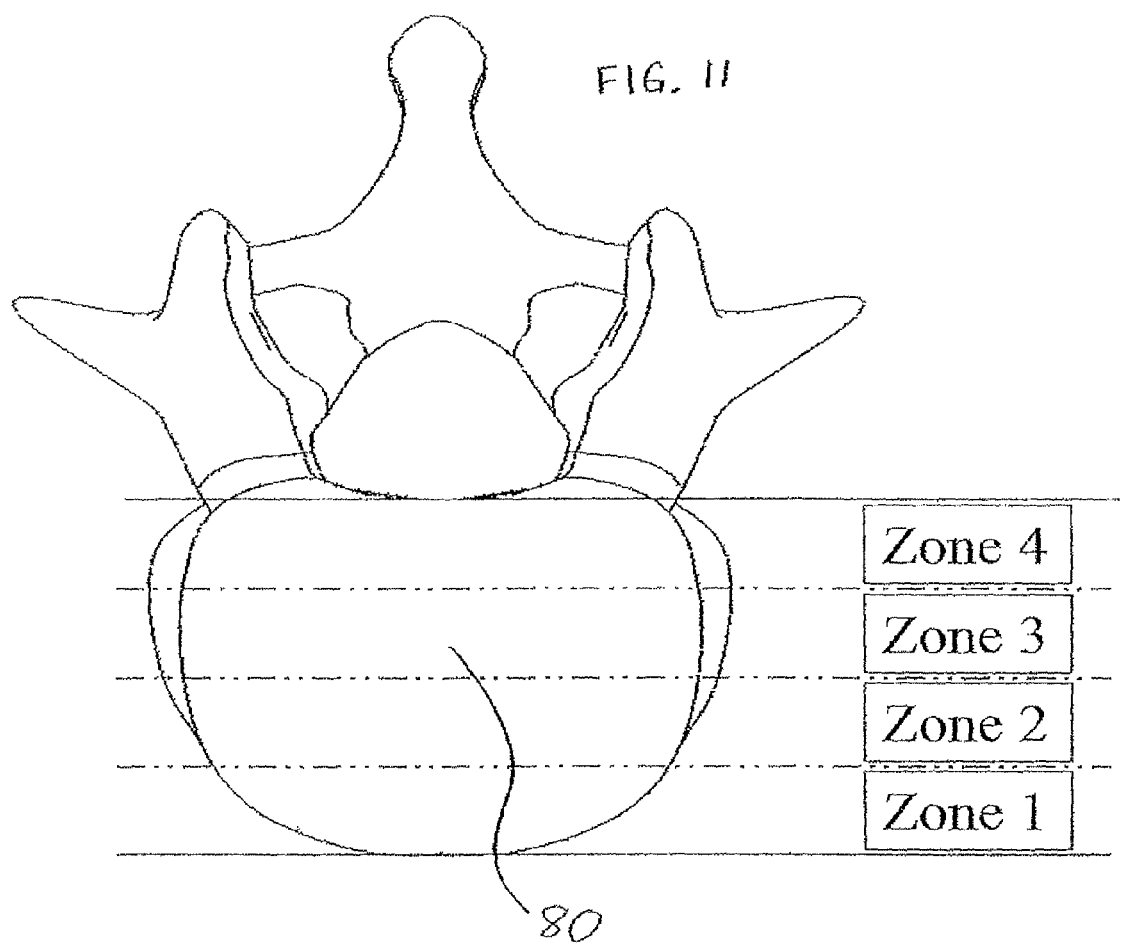
FIG. 11 is a top view of a vertebra showing the vertebral body divided into four equal zones.

As shown in FIG. 11, in the lumbar vertebral, the area between the anterior and posterior edges of the vertebral body (VB) 80 may be divided into four equal zones. As shown by the flow chart of FIG. 16, the present invention may be described as a method 100 of implanting an implant 10 into a body. Method 100 may have a step 110 of inserting the implant into an anterior portion of the body using lateral access while the implant is in a straightened or low curvature state, as shown in FIG. 12. The implant may have a backbone 30 and a deflectable piece 20 meeting (i.e. interconnected to or abutting) the backbone at a distal end 22 of the deflectable piece. The backbone 30 may be positioned, in a preferred embodiment, on the vertebral lips (apophyseal ring) or within the confines of the annulus. The deflectable piece 20 used in this method (and other methods) may be comprised of a sequence of segments 40 and in general may be structured as described above for implant 10.

Method 100 may also have a step 120 of deploying the implant, for example posteriorly, by deflecting the deflectable piece, as shown in FIG. 13. For example, step 110 may involve inserting the implant onto zone two of the intervertebral disc and step 120 may involve deploying the deflectable piece posteriorly onto zone three and/or zone four of the intervertebral disc.

The deflecting of deflectable piece 20 may deflect implant 10 into an asymmetric, for example D-shaped, loop by applying longitudinal pressure to the proximal end of the deflectable piece or by applying longitudinal pressure to the backbone 30 to pull the backbone. In either case, this may generate relative longitudinal movement between the proximal end and at least a distal end of the backbone and may generate an outward horizontal movement of at least a portion (for example a central portion) of the deflectable piece away from the backbone. As shown in FIGS. 12-13, this deflection may be accomplished without a tensioning element and without a mechanical linkage. For example, as shown in FIG. 12-13, the application of longitudinal pressure may be achieved by using a pusher/deployer to apply longitudinal pressure to a proximal end (which may be a proximal segment) of the deflectable piece after insertion. Deflecting the deflectable piece by applying longitudinal pressure to a proximal end of the deflectable piece or to a proximal end of the backbone (for example in an opposite direction for example by pulling the backbone) may generate relative longitudinal movement between the proximal end of the deflectable piece 20 and at least a distal end of the backbone and move at least a portion of the deflectable piece away from the backbone. Furthermore, if deflectable piece 20 is made up of segments 40 with cut-outs, then deflecting the implant into an asymmetric loop, such as a D-shaped loop, by applying the longitudinal pressure to the proximal end 24 of deflectable piece 20 (or to the backbone in an opposite direction) to generate relative longitudinal movement between the backbone and the proximal end 24 may close or partially close cut-outs between segments of a sequence of segments of the deflectable piece, as shown in FIGS. 3-4. By setting an initial position of the backbone the user may be able to pre-define a final position of the implant in a deflected state.

After deflection, the holder and deployer may be separated and removed from the implant in a separate step. The implant device would then remain between the vertebral body shown in the FIGS. 11-13 and the one above it (not shown).

Figure 17:
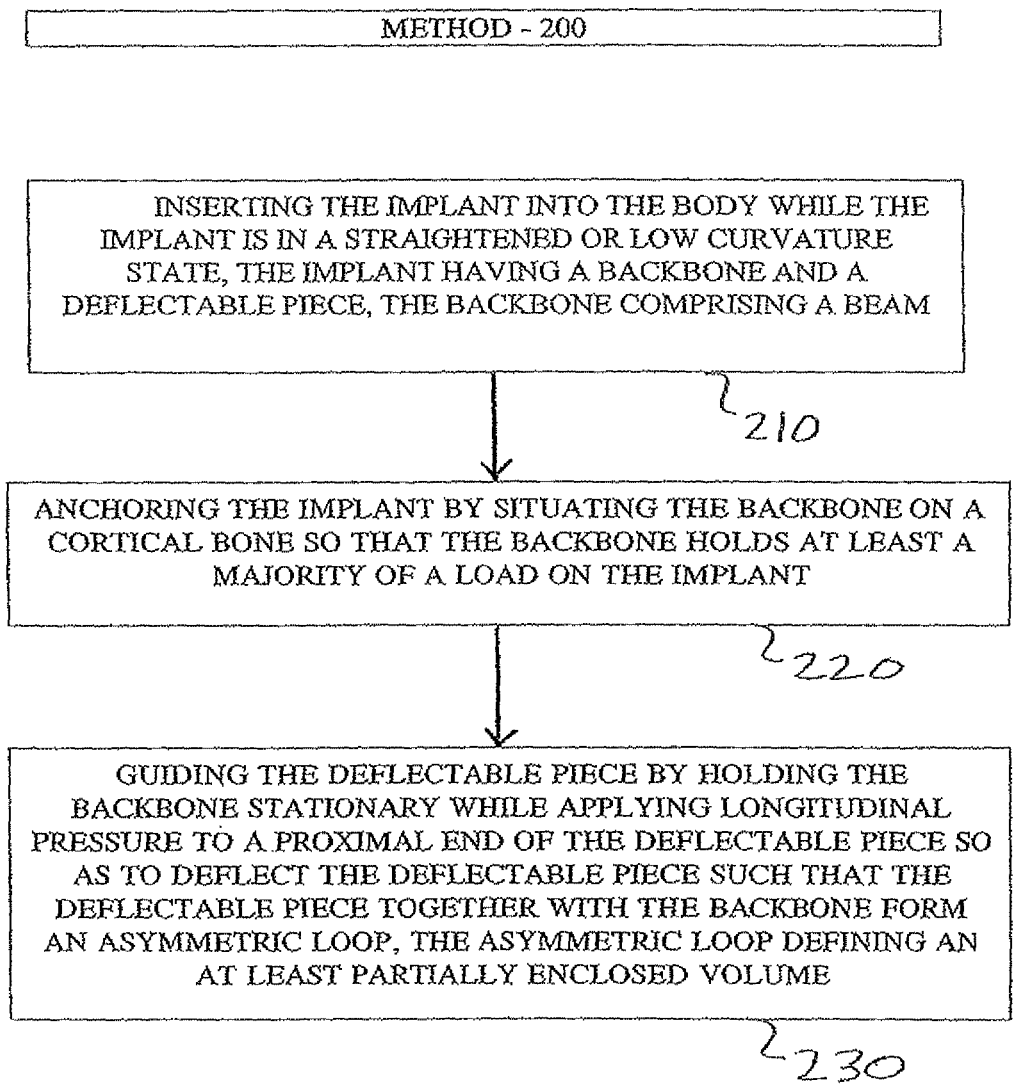
FIG. 17 is a flow chart showing a further method in accordance with one embodiment of the present invention.

As shown by the flow chart of FIG. 17, the present invention may also be described by a further method 200 of implanting an implant into a body. Method 200 may involve a step 210 of inserting the implant into the body while the implant is in a straightened or low curvature state, the implant having a backbone and a deflectable piece, wherein the backbone comprises a beam. Method 200 may also have a step 220 of anchoring the implant by situating the backbone 30 on a cortical bone so that the backbone holds at least a majority of a load of the implant, or in other preferred embodiments at least two-thirds of the load. In order to accomplish this (or for other reasons) method 200 may also involve configuring the backbone so that a height of the backbone is at least a maximum height of the deflectable piece. To allow the backbone to carry the desired load, method 200 may involve configuring the backbone so that a width of the backbone is at least half as large as a height of the backbone, or configuring the backbone so that a width of the backbone is at least three-quarters as large as a height of the backbone, or configuring the backbone as a solid beam (or a solid beam with openings appropriate for delivery of biocompatible material or instruments). Method 200 (or any of the other methods herein) may also involve a further step of inserting a biocompatible material into the at least partially enclosed volume through a window in the implant.

Step 230 may involve guiding the deflectable piece by causing relative longitudinal movement between a proximal end of the deflectable piece and the backbone either by holding the backbone stationary while applying longitudinal pressure to a proximal end of the deflectable piece or by pulling the backbone while the deflectable piece is stationary or by closing a telescoping backbone. This may deflect the deflectable piece such that the deflectable piece together with the backbone form an asymmetric loop, for example a D-shaped loop, the asymmetric loop defining an at least partially enclosed volume.

As shown by the flow chart of FIG. 18, the present invention may also be described as a further method 300 of implanting an implant into a body. Method 300 may include a step 310 of inserting the implant into a portion of the body while the implant is in a straightened or low curvature state, the implant having a backbone and a deflectable piece, for example comprising a sequence of segments interconnected at effective hinges. A further step 320 may involve having a distal end (for example a distal segment) of the sequence meet the backbone (i.e. by abutting or being interconnected to the backbone) at a distal end of the deflectable piece. This may occur prior to insertion (with the backbone or after insertion of the implant. A further step 330 may involve deploying the implant so as to form a loop between the backbone and deflectable piece together by deflecting the deflectable piece such that a proximal end of the deflectable piece moves longitudinally relative to at least a distal end of the backbone (by either applying longitudinal pressure to the proximal end, for example while holding the backbone stationary, or by pulling the backbone for example while holding the proximal end stationary or for example by closing a telescoping backbone). The proximal end may also interconnect to the backbone.

In some preferred embodiments, method 300 may also have a step of inserting the implant onto an intervertebral disc using lateral access to the disc and then deploying the implant posteriorly if the implant was inserted onto an anterior portion of the disc and anteriorly if the implant was inserted onto the posterior portion of the disc. It should be fully understood, however, that in other preferred embodiments, an approach other than lateral access may be used to insert the implant into the body.

Method 300 may also have a step of locking the implant to prevent undesired motion of the deflectable piece relative to the backbone. Another step of method 300 may be applying longitudinal pressure to a proximal segment of a sequence of segments comprising the deflectable piece so as to deflect the deflectable piece such that the deflectable piece together with the backbone form an asymmetric loop such as D-shaped loop, the asymmetric loop defining an at least partially enclosed volume. Method 300 may involve a step of configuring the backbone so that a width of the backbone is at least half as large as a height of the backbone, or in other preferred embodiments at least two-thirds as large, at least three-quarters as large, at least equal to, or between half and one and a half the height. Method 300 may also involve deploying the implant while the backbone is maintained stationary along an axis defined by a direction of insertion.

Figure 22A:
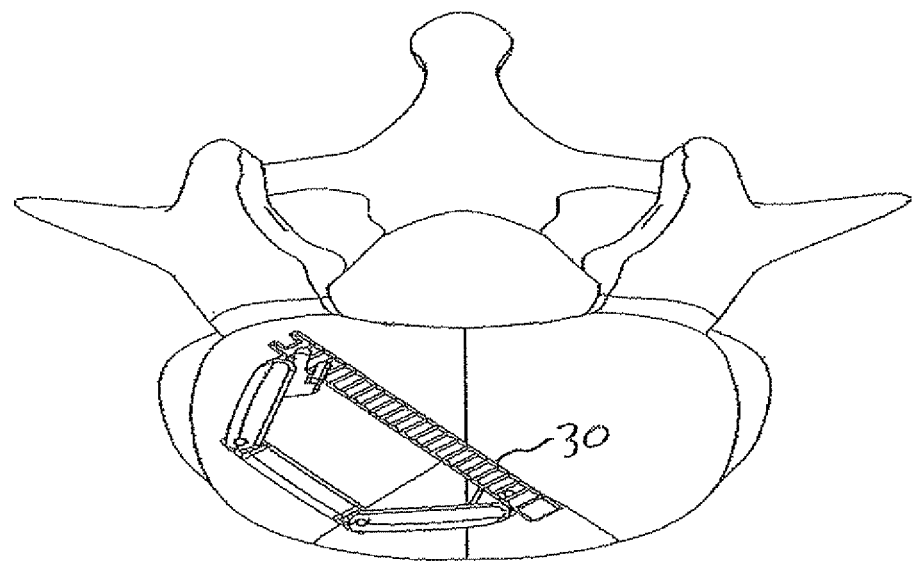
FIG. 22A shows a laterally deflectable implant inserted through a TLIF approach, in accordance with one embodiment of the present invention.

As shown by the flow chart of FIG. 19 and the device shown in FIG. 22, the present invention may also be described as a method 400 of implanting implants into a body. Method 400 may have a step 410 of inserting into the body a first laterally deflectable implant that has a first backbone and a first deflectable piece while the first deflectable piece is in a straightened or low curvature insertion state. A further step 420 may be inserting into the body a second laterally deflectable implant that has a second backbone and a second deflectable piece while the second deflectable piece is in a straightened or low curvature insertion state and such that the first and second backbones are between the first and second deflectable pieces. In a preferred embodiment, the second laterally deflectable implant is inserted into the body such that the first backbone and the second backbone are substantially parallel. "Substantially parallel" is defined to mean parallel or within 20 rotational degrees of being perfectly parallel. In a preferred embodiment, the first and second backbones are within five rotational degrees (or ten rotational degrees or fifteen rotational degrees in other preferred embodiments) of being perfectly parallel. In a preferred embodiment, the inserting of the first and second laterally deflectable implants in the body may be implemented so that the first and second backbones are between the first and second deflectable pieces, as shown in FIG. 22.

Method 400 may also involve a step 430 of deflecting the first and second laterally deflectable implants in opposite directions such that the first laterally deflectable implant defines a first asymmetric loop (which may be D-shaped), said first asymmetric loop defines an at least partially enclosed volume and such that the second laterally deflectable implant defines a second asymmetric loop (which may be D-shaped), said second asymmetric loop defines an at least partially enclosed volume. In one preferred embodiment, the shapes of the first and second asymmetric loops are the same (i.e. D-shaped and D-shaped, rectangular and rectangular, etc.) although in other preferred embodiments, one can be D-shaped and the other rectangular or another asymmetric shape.

A further step of method 400 may be generating relative longitudinal movement between at least a distal end of the first backbone and a proximal end of the first deflectable piece to deflect the first deflectable piece and generating relative longitudinal movement between at least a distal end of the second backbone and a proximal end of the second deflectable piece to deflect the second deflectable piece.

Figure 22B:
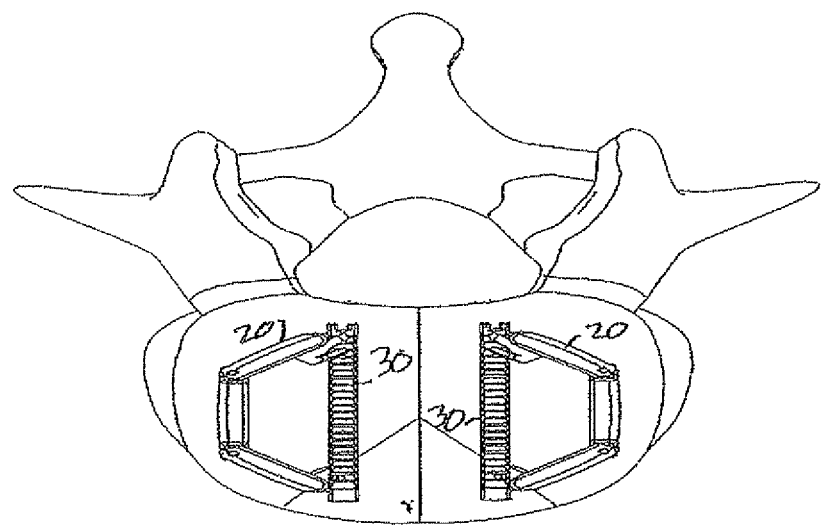
FIG. 22B shows two laterally deflectable asymmetric implants alongside one another resulting from a PLIF insertion approach, in accordance with one embodiment of the present invention.

Method 400 may be useful for two implants inserted in parallel fashion through a PLIF, as shown in FIG. 22B.

Figure 23A:
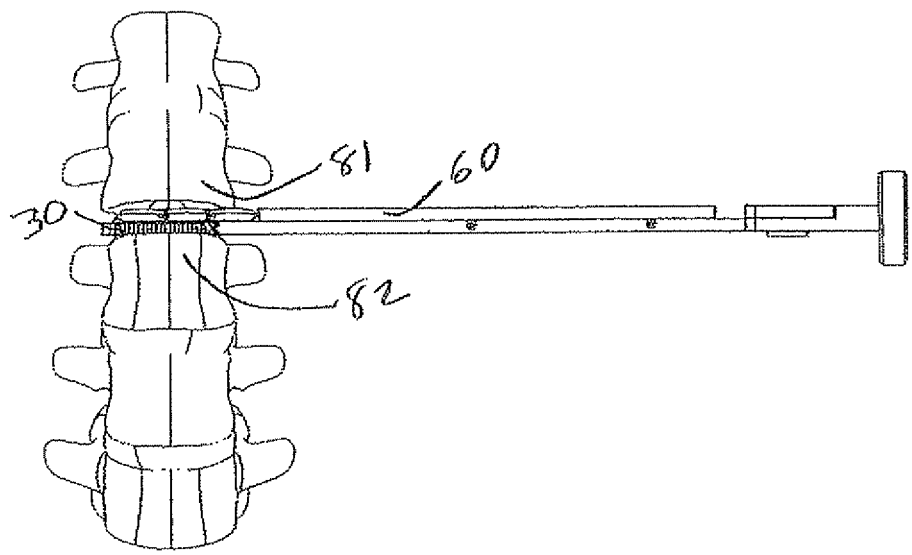
FIGS. 23A-B are side views of an implant, holder and deployer effectuating vertical distraction of the intervertebral space between endplates, in accordance with one embodiment of the present invention.
Figure 23B:
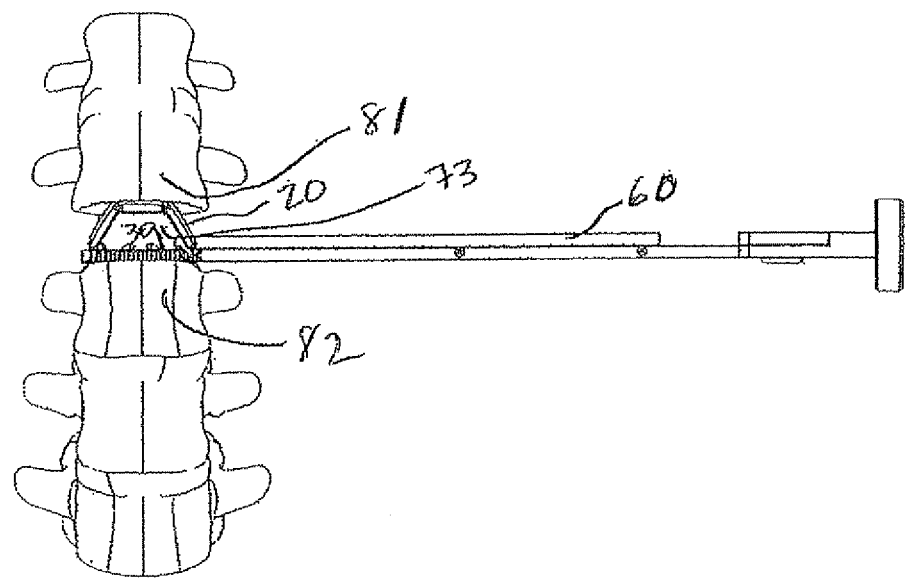

Furthermore, as shown by the flow chart of FIG. 20 and the device shown in FIGS. 23A-B, the present invention may also be described as a method 500 of distracting intervertebral space 73 between discs or between a first and a second vertebrae 81, 82. Method 500 may have a step 510 of inserting an implant 10 structured as described herein into a body while the implant 10 is in a straightened or low curvature state, the implant having a backbone 30 and a deflectable piece 20 meeting the backbone (interconnected or abutting).

In other preferred embodiments, instead of inserting implant 10, step 510 may involve inserting an instrument assembly including an element having the structure of implant 10 (although by right it is not called an implant since it is not implanted into the body but rather inserted and removed), together with an integrally formed deployer and a holder. This instrument assembly would be removed after distraction is performed and its purpose may have been merely to assess the size of a possible distraction involving an implant.

Method 500 may have a further step 520 of generating relative longitudinal movement between a proximal end of the deflectable piece and at least a distal end of the backbone so as to deflect the deflectable piece and distract an intervertebral space between the first and second vertebrae (i.e. between adjacent first and second vertebrae).

Method 500 may also have a step of inserting the implant into the body such that the backbone of the implant is abutting or facing an endplate of one vertebra (of the first and second vertebra) and the deflectable piece is abutting or facing an endplate of another vertebra (of the first and second vertebrae). This may be implemented by for example inserting the implant 10 vertically into a vertebral body that has collapsed and the using step 520 to generate relative longitudinal movement between a proximal end of the deflectable piece and at least a distal end of the backbone so as to deflect the deflectable piece and distract endplates of the same vertebra (such as to restore vertebral height in VCF). For example, prior to inserting the implant, the implant may be configured so that upon insertion the implant is already oriented vertically such that the backbone is abutting or facing an endplate of one vertebra and the deflectable piece is abutting or facing an endplate of a second vertebra.

The relative longitudinal movement may be generated using application of longitudinal pressure, for example against the proximal end 24 or against the backbone, for example as described herein, or using another method described herein. In a preferred embodiment of method 500, the deflecting of the deflectable piece is such that the backbone together with the deflectable piece defines an asymmetric loop, the asymmetric loop defining an at least partially enclosed loop.

The deflectable piece of the implant may be deflected in any of the manners that are described herein.

Figure 26A:
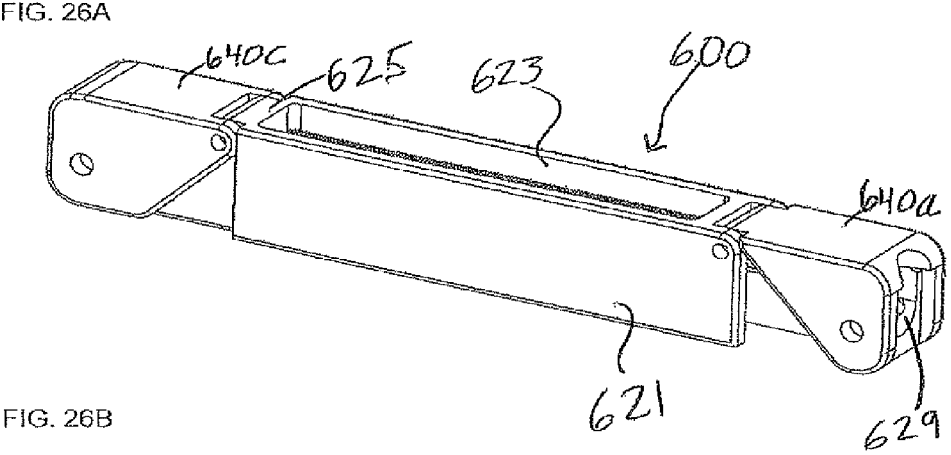
FIG. 26A is an isometric view of an implant whose undeflected deflectable piece includes side panels useful for vertical distraction, in accordance with one embodiment of the present invention.
Figure 26B:
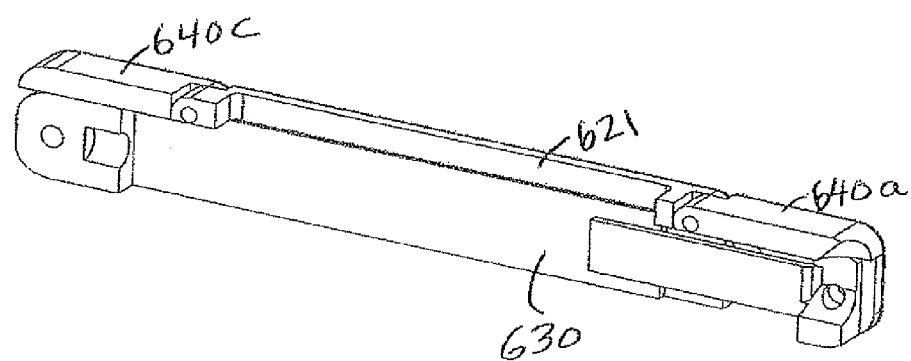
FIG. 26B is a vertical sectional view of the implant of FIG. 26A, in accordance with one embodiment of the present invention.
Figure 26C:
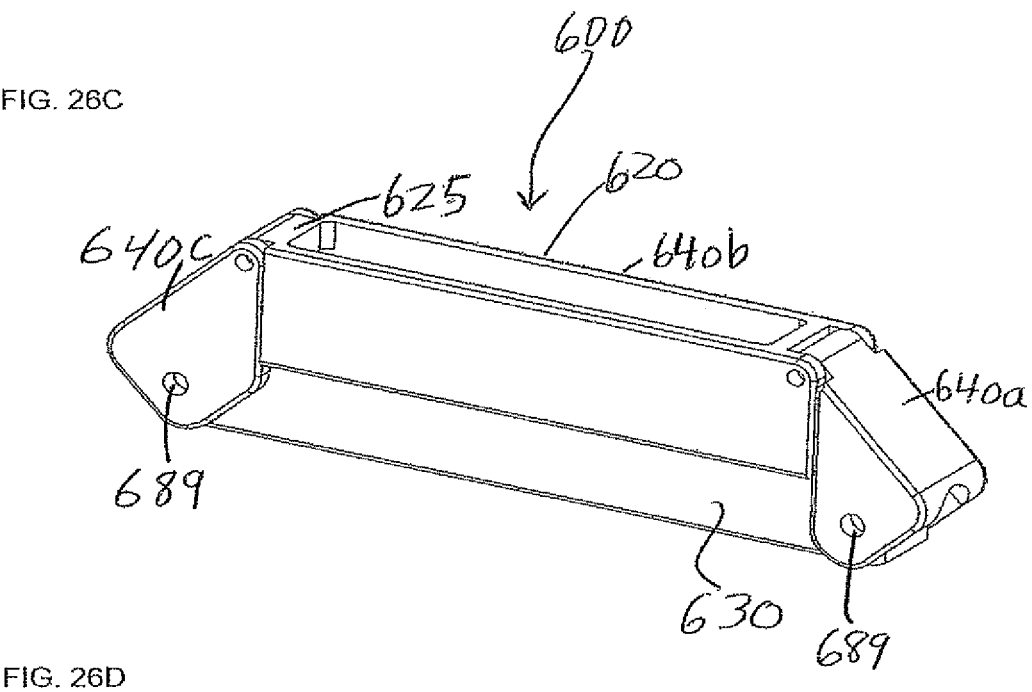
FIG. 26C is an isometric view of the implant of FIG. 26A after deflection of the deflectable piece, in accordance with one embodiment of the present invention.

In order to distract the intervertebral space (i.e. increase the distance) between the first and second vertebra, since the implant 600 is oriented vertically, in some preferred embodiments as shown in FIGS. 26A-D, the deflectable piece may incorporate side panels 621 to help define the at least partially enclosed volume. Side panels 621 may extend from deflectable piece 620 (for example from a middle segment or from a segment that is not a first or last segment of deflectable piece 620) to backbone 630 and may overlap with the backbone 630 to form a continuous enclosure for the at least partially enclosed volume. In FIG. 26C, the side panels 621 may overlap the sides 631, 634 of backbone 630 (which sides in the horizontal orientation of implant 10 are referred to as the top surface 31 and bottom surface 34 of backbone 30) whereas in the deflected configuration shown in FIG. 26B the side panels 621 may overlap only a portion (in the vertical dimension for example between vertebra) of sides 631, 634 of backbone 30. This is sufficient to form the at least partially enclosed volume, and in particular to form a hollow chamber defined by the backbone and by the deflectable piece or a portion (for example a middle segment) of the deflectable piece. Accordingly, after deflection of the deflectable piece, backbone 630 of implant 600 may be abutting or facing an endplate of one vertebra of the first and second vertebra and deflectable piece 620 may be abutting or facing an endplate of another vertebra of the first and second vertebra. Furthermore, backbone 630 and deflectable piece 620 together may form, after deflection of the deflectable piece, a chamber that is enclosed other than on a surface facing an endplate of one vertebra of the first and second vertebra and other than on a surface facing an endplate of another vertebra of the first and second vertebra. In contrast to this embodiment, note that in the horizontally oriented embodiments of implant 10 the "sides" of the implant 10 are normally covered by the endplates or other bodily material of the body of the subject.

An opening in a surface of the deflectable piece and an opening in a surface of the backbone may define an unobstructed path between the deflectable piece and backbone through the at least partially enclosed volume. For example, as can be seen from FIGS. 26A-D, there may be an unobstructed or direct path from an opening 623 in a top surface 625 of a middle segment 40b of deflectable piece 20 to an opening in a bottom surface of backbone 30. This direct path or passage is useful where fusion is employed since it may allow fusion of bone or other biocompatible material with endplates of adjacent vertebrae. For clarity, it is noted that the bottom surface of backbone 630 would be called the rear surface in embodiments showing the implant 10 in a horizontal orientation. In addition, "top" surface 625 is called "top" by reference to the vertical orientation shown in FIGS. 26A-D yet it corresponds to side surface 25 of middle segment 40b in the implant 10 of FIG. 2 which depicts an implant 10 in the horizontal orientation.

It is emphasized that FIGS. 26A-D happen to show the vertically oriented implant with the side panels in the context of a telescoping backbone 630 and a deflectable piece 620 having three segments, 640a, 640b, 640c, but none of these features (that the backbone 630 is telescoping, that the deflectable piece 620 is segmented and that the deflectable piece 620 has three segments rather than two, four, five, etc.) are required aspects of this embodiment. If for example deflectable piece 630 is segmented, the opening in the top surface of deflectable piece 630 would normally be in the top surface of a segment other than the first and last segment, although this is not a required limitation either. Furthermore, the vertically oriented embodiment of the implant may define a loop that is not a strict loop as defined herein (i.e. may have a gap) and may incorporate any other suitable feature described in the context of other embodiments.

Figure 26D:
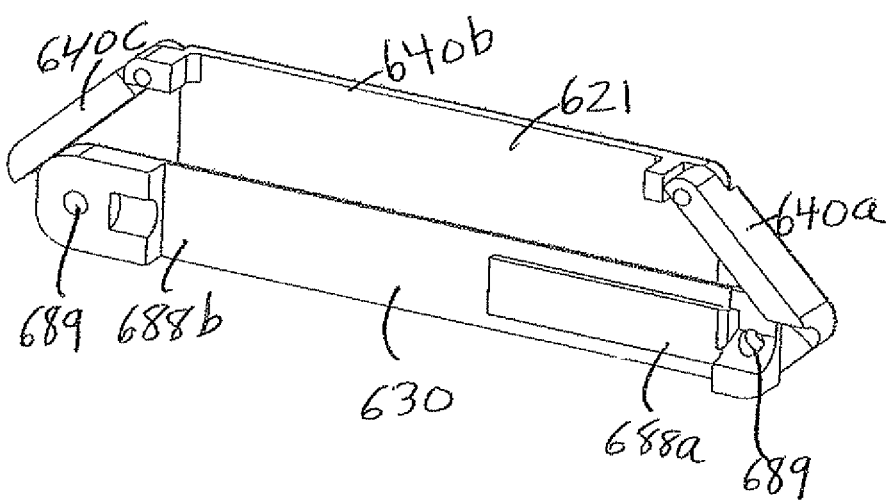
FIG. 26D is a vertical sectional view of the implant as shown in FIG. 26C, in accordance with embodiment of the present invention.

As shown in FIG. 26A, moreover, a first segment 640a may have a hole 629 for insertion of biocompatible material such as bone graft, autograft, allograft, etc. Furthermore, as shown in FIGS. 26C-D, the two telescoping portions 688a, 688b of the telescoping backbone 630 may have one or more holes 689 and/or threading to interface with a holder 650 and/or deployer 660 mechanism or instrument such as described herein with respect to implant 10 (see FIGS. 5A-6).

Figure 24A:
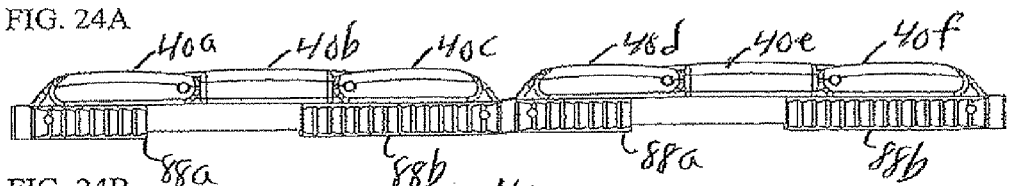
FIGS. 24A-B are top isometric views of an implant with two sequences of segments each with adjustable backbones, before and after deflection, in accordance with one embodiment of the present invention.
Figure 24B:
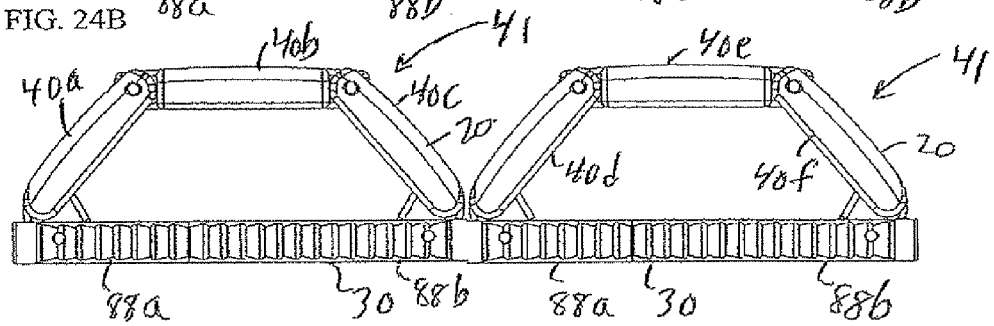
Figure 24C:
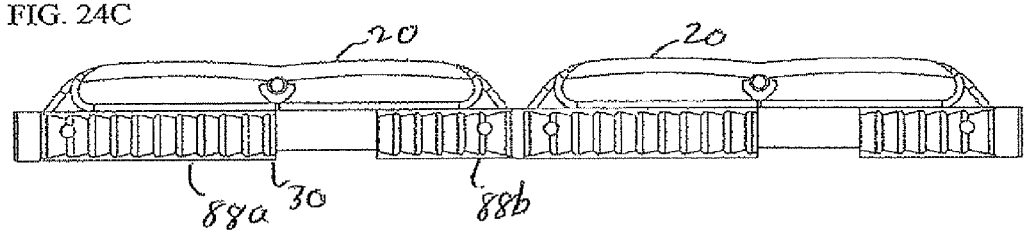
FIGS. 24C-E are top isometric views of an implant whose deflectable piece has two sequences of segments each deflected separately and independently using adjustable length backbones, in accordance with one embodiment of the present invention.
Figure 24D:
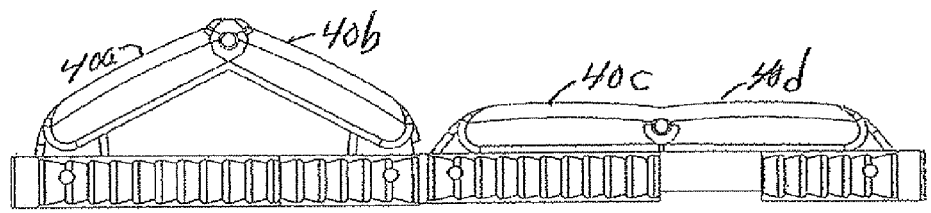
Figure 24E:
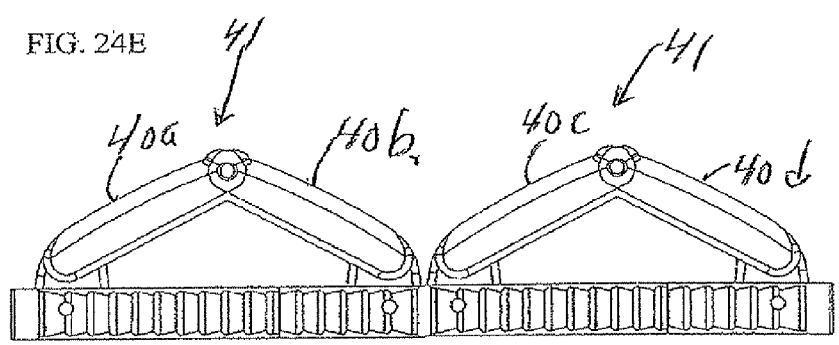

In a still further method of the present invention shown in FIGS. 24C-E, in which deflectable piece 20 is comprised of at least four segments 40, the deflection of deflectable piece 20 may occur separately with respect to two sequences 41 of segments 40. As shown in FIG. 24C, implant and deflectable piece 20 are initially straight, for example for insertion. As shown in FIG. 24D, the two most proximal segments 40a, 40b forming a first sequence 41 of segments 40 are then deflected, for example by actuating the telescoping feature of backbone 30 (or in other preferred embodiments by applying longitudinal pressure to a proximal end 40c c (see FIG. 2) of segment 40c or possibly by pulling backbone 30). More distal segments 40c, 40d remain straight. As shown in FIG. 24E, deflection of segments 40c, 40d forming a second sequence 41 of segments 40 may then be effectuated by applying longitudinal pressure or actuating the telescoping feature. In the implant depicted in FIGS. 24C-E, backbone 30 is telescoping and is of adjustable length. Hence, the deflection may be generated by application of longitudinal pressure, such as against a proximal end 32 of backbone 30 or by an internal mechanism of backbone 30 that actuates the telescoping of backbone 30.

FIGS. 24A-B are similar to FIGS. 24C-E except that in FIGS. 24A-B, each sequence 41 of segments of the deflectable piece 20 has three interconnected segments rather than two. In addition, the telescoping of the backbone 30 in FIGS. 24A-B of each sequence may derive from a common actuator deflecting simultaneously or may be actuated and deflected separately whereas in FIGS. 24C-E, the deflection of the separate sequences 41 are necessarily occurring separately.

As shown by FIGS. 27A-K, the present invention may also involve a method of implanting an implant comprising inserting a holder shaft 92 into an implant 10 of the kind shown in FIGS. 27A-K. The method may also have a step of attaching a deployment tube 91 to the rear of the rotatable element (i.e. the threaded tube 93). A further step may involve deflecting the implant by actuating (i.e. rotating) the deployment tube 91 so as to rotate the rotatable element 93, thereby advancing the rotatable element longitudinally/axially relative to the annular element (i.e. threaded nut). Since the rotatable element is attached to (or abutting) the proximal part of the deflectable piece, the deflectable piece may move longitudinally relative to at least a distal end of the backbone. In another step, after deflection of the implant 10, the user may then disconnect the deployment tube 91. The user may also then disconnect the holder shaft 92.

It should be understood that one or more steps of the methods described herein may be combined. Furthermore, any suitable embodiment of implant 10 described herein consistent with the steps of a particular method may be used in any such method. It should also be understood that the term "backbone" 30 used as an element of the implant 10 is not related in meaning to the "backbone" of a spine of a person into which such an implant may, in some embodiments, be implanted.

As noted, in general the methods and apparatus of the present invention are not limited to insertion of the implant through lateral access into the body, and other insertion routes may be used, for example through the back as in posterior lumbar interbody fusion (PLIF) or transforaminal lumbar interbody fusion (TLIF). Furthermore, the term "laterally" in the phrase "laterally deflectable implant" has no connection or relation with the route of insertion such as insertion through "lateral" access. In fact, the direction of the lateral access is along the direction of insertion of the implant and this direction is considered to be longitudinal as discussed herein. Rather, "laterally deflectable" refers to a direction of the deflection of the deflectable piece 20 and imposes no limitation as to whether the implant deflects in the horizontal or vertical orientation.

Furthermore, the terms "vertical" and "vertically" as used herein refer to the orientation in either a sagittal plane, a plane parallel to the sagittal plane, a frontal/coronal plane or a plane parallel to the frontal/coronal plane (the exception being the term "vertical sectional view" in the Brief Description of the Drawings which has its ordinary meaning in relation to the view of the implant or other structure). The terms "horizontal orientation", "horizontally oriented", in contrast, refer to horizontal or transverse planes perpendicular to the "vertical", as used herein. Accordingly, this patent application describes an implant that may be deflectable in the horizontal orientation but may also be deflectable in the vertical orientation for example when used for vertical distraction.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. An expanding implant for insertion between two regions of tissue, the implant comprising:
   a base having a contact surface for contacting a first region of tissue, said base comprising a proximal portion in sliding engagement with a distal portion, said base assuming an initial length and being shortened towards a second length when said proximal portion slides towards said distal portion;
   a first rigid linking segment hingedly connected to a distal region of said distal portion of said base for relative rotation about a single pivot axis relative to said distal portion of the base;
   a second rigid linking segment hingedly connected to a proximal region of said proximal portion of said base; and
   an intermediate portion having a contact surface for contacting a second region of tissue, said contact surface of said intermediate portion spanning a majority of said second length, said intermediate portion being hingedly connected to said first linking segment and to said second linking segment such that shortening of said base from said initial length towards said second length causes an increase in a distance between said contact surfaces of said base and said intermediate portion, and wherein said intermediate portion and said base are each formed with openings through said respective contact surfaces such that each of said contact surfaces is open along a majority of its length, said openings providing at least one unobstructed path between the first and second regions of tissue.

2. The expanding implant of claim 1, wherein said intermediate portion is implemented as a rigid intermediate segment.

3. The expanding implant of claim 2, wherein said intermediate segment and said base are formed with regions of overlap, and wherein said regions of overlap are sufficient to maintain overlap between said intermediate segment and said base during said increase in distance between said contact surfaces.

4. The expanding implant of claim 2, wherein at least one of said second linking segment and said proximal portion of said base is formed with an aperture to allow insertion of filling material into the implant along a direction of elongation of the implant.

5. The expanding implant of claim 1, wherein at least one of said second linking segment and said proximal portion of said base is formed with an aperture to allow insertion of filling material into the implant along a direction of elongation of the implant.

6. The expanding implant of claim 1, further comprising:
   (a) a shaft engagable with said distal portion of said base and extending along said base so as to project from the implant in a proximal direction; and
   (b) a deployment element cooperating with the proximal portion of said base,
wherein advancing of said deployment element relative to said shaft is effective to deploy said proximal portion of said base towards said distal portion of said base.

7. The expanding implant of claim 6, wherein said deployment element is implemented as a tube enclosing a proximal portion of said shaft.

8. The expanding implant of claim 7, wherein said tube is in threaded engagement with said proximal portion of said shaft such that rotation of said deployment tube relative to said shaft is effective to advance said tube, thereby displacing said proximal portion of said base towards said distal portion of said base.

9. The expanding implant of claim 1, further comprising a locking arrangement deployed to retain a shortened state of said base, thereby maintaining an expanded state of the implant.

10. The expanding implant of claim 1, wherein said contact surfaces of said base and said intermediate portion are substantially parallel.

11. A method comprising the steps of:
    (a) in a surgical procedure, deploying within a spinal column an expanding spinal implant comprising:
        a base having a contact surface for contacting a first region of tissue, said base comprising a proximal portion in sliding engagement with a distal portion, said base assuming an initial length and being shortened towards a second length when said proximal portion slides towards said distal portion;
        a first linking segment hingedly connected to a distal region of said distal portion of said base for relative rotation about a single pivot axis relative to said distal portion of the base;
        a second linking segment hingedly connected to a proximal region of said proximal portion of said base; and
        an intermediate portion having a contact surface for contacting a second region of tissue, said intermediate portion being hingedly connected to said first linking segment and to said second linking segment such that shortening of said base from said initial length towards said second length causes an increase in a distance between said contact surfaces of said base and said intermediate portion, thereby increasing a spacing between the first and second regions of tissue
        the expanding spinal implant being deployed with said contact surfaces of said base and said intermediate portion facing first and second regions of tissue, respectively;
    (b) shortening said base from said initial length towards said second length, thereby increasing a distance between said contact surfaces of said base and said intermediate portion so as to increase a spacing between the first and second regions of tissue; and
    (c) leaving said spinal implant within the spinal column after termination of the surgical procedure as an implant.

12. The method of claim 11, wherein:
    (a) said first and second regions of tissue are opposing vertebral endplates facing an intervertebral space; and
    (b) said shortening said base from said initial length towards said second length increases a spacing between the opposing vertebral endplates.

13. The method of claim 12 further comprising introducing filling material into an internal volume of said expanding spinal implant so as to promote interbody fusion.

14. The method of claim 12, wherein said step of deploying is performed via a PLIF approach.

15. The method of claim 12, wherein said step of deploying is performed via a TLIF approach.

16. The method of claim 12, wherein said step of deploying is performed via a lateral approach.

17. The method of claim 12, wherein said spinal implant is referred to as a first spinal implant, the method further comprising deploying a second expanding spinal implant so as to provide support in two regions between the opposing vertebral endplates.

18. An expanding implant for insertion between two regions of tissue, the implant comprising:
    a base having a contact surface for contacting a first region of tissue, said base comprising a proximal portion in sliding engagement with a distal portion, said base assuming an initial length and being shortened towards a second length when said proximal portion slides towards said distal portion;
    a first rigid linking segment directly hingedly connected to a distal region of said distal portion of said base;
    a second rigid linking segment hingedly connected to a proximal region of said proximal portion of said base; and
    an intermediate portion having a contact surface for contacting a second region of tissue, said contact surface of said intermediate portion spanning a majority of said second length, said intermediate portion being hingedly connected to said first linking segment and to said second linking segment such that shortening of said base from said initial length towards said second length causes an increase in a distance between said contact surfaces of said base and said intermediate portion, and wherein said intermediate portion and said base are each formed with openings through said respective contact surfaces such that each of said contact surfaces is open along a majority of its length, said openings providing at least one unobstructed path between the first and second regions of tissue.

* * * * *